United States Patent
Goldstein et al.

(10) Patent No.: US 9,676,778 B2
(45) Date of Patent: Jun. 13, 2017

(54) SUBSTITUTED PYRROLO[2,3-B]PYRAZINES AS JAK3 INHIBITORS

(71) Applicant: PRINCIPIA BIOPHARMA INC., South San Francisco, CA (US)

(72) Inventors: David Michael Goldstein, Redwood City, CA (US); Kenneth Albert Brameld, Menlo Park, CA (US); Tim Owens, San Carlos, CA (US)

(73) Assignee: PRINCIPIA BIOPHARMA INC., South San Francisco, CA (US)

( * ) Notice: Subject to any disclaimer, the term of this patent is extended or adjusted under 35 U.S.C. 154(b) by 89 days.

(21) Appl. No.: 14/443,705

(22) PCT Filed: Nov. 19, 2013

(86) PCT No.: PCT/US2013/070834
§ 371 (c)(1),
(2) Date: May 19, 2015

(87) PCT Pub. No.: WO2014/081732
PCT Pub. Date: May 30, 2014

(65) Prior Publication Data
US 2015/0291600 A1 Oct. 15, 2015

Related U.S. Application Data

(60) Provisional application No. 61/728,539, filed on Nov. 20, 2012.

(51) Int. Cl.
*A61K 31/4985* (2006.01)
*C07D 487/04* (2006.01)
*C07D 471/04* (2006.01)
*A61K 45/06* (2006.01)

(52) U.S. Cl.
CPC ........ *C07D 487/04* (2013.01); *A61K 31/4985* (2013.01); *A61K 45/06* (2013.01); *C07D 471/04* (2013.01)

(58) Field of Classification Search
CPC ................ A61K 31/4985; C07D 487/04

USPC .......................................... 514/249; 544/350
See application file for complete search history.

(56) References Cited

FOREIGN PATENT DOCUMENTS

WO  WO 2010/129567 A1  11/2010
WO  WO 2014/081732  *  5/2014

OTHER PUBLICATIONS

Jordan, V. C. Nature Reviews: Drug Discovery, 2, 2003, 205.*
Dorwald, F. Zaragoza. Side Reactions in Organic Synthesis: A Guide to Successful Synthesis Design, Weinheim: WILEY-VCH Verlag GmbH & Co. KGaA, 2005, Preface.*
Hackam, et al. JAMA, 296(14), 2006, 1731-1732.*
PCT Notification of Transmittal of the International Search Report and the Written Opinion of the International Searching Authority, or the Declaration in International Application No. PCT/US2013/070834, mailed Jan. 16, 2014 (8 pages).

* cited by examiner

*Primary Examiner* — Douglas M Willis
(74) *Attorney, Agent, or Firm* — Finnegan, Henderson, Farabow, Garrett & Dunner, LLP

(57) ABSTRACT

The present disclosure provides compounds of formula (I)

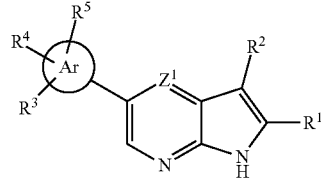

wherein the variables are as defined herein that are JAK3 inhibitors and therefore useful for the treatment of diseases treatable by inhibition of JAK3 such as cancer and inflammatory diseases. Also provided are pharmaceutical compositions containing such compounds and processes for preparing such compounds.

24 Claims, No Drawings

SUBSTITUTED PYRROLO[2,3-B]PYRAZINES AS JAK3 INHIBITORS

CROSS-REFERENCE TO RELATED APPLICATIONS

This application is a national phase application based on international application number PCT/US2013/070834, filed Nov. 19, 2013, and claims the benefit of provisional application No. 61/728,539, filed Nov. 20, 2012, the content of each application being incorporated herein by reference.

The present disclosure provides compounds that are JAK3 inhibitors and therefore useful for the treatment of diseases treatable by inhibition of JAK3 such as cancer and inflammatory diseases. Also provided are pharmaceutical compositions containing such compounds and processes for preparing such compounds.

JAK3 is a cytoplasmic tyrosine kinase that functions downstream of the common gamma chain receptor subunit for cytokine signaling. It is crucial for signal transduction in response to stimulation by IL-2, IL-4, IL-5, IL-7, IL-9, and IL-21 (see Shuai K and Liu B. Regulation of JAK-STAT signaling in the immune system. *Nat Rev Immunol.* 3:900-11. 2003 and O'Shea J. J, et al. A new modality for immunosuppression: targeting the JAK/STAT pathway. *Nat Rev Drug Discov.* 3:555-64. 2004). The expression of JAK3 is restricted to mainly lymphoid and myeloid cells in contrast to the other Jak family members, which are more ubiquitously expressed (see Johnston J A, et al. Phosphorylation and activation of the Jak-3 Janus kinase in response to interleukin-2. *Nature.* 370:151-3. 1994). This makes JAK3 an attractive target for immunosuppression. JAK3 null humans have a severe combined immunodeficiency disease (SCID). These individuals display lack of circulating T and NK cells with normal numbers of B cells (see Pesu M, et al. JAK3, severe combined immunodeficiency, and a new class of immunosuppressive drugs. *Immunol Rev.* 203:127-42. 2005). In mice, JAK3 deficiency results in not only T and NK cell depletion, but B cells as well (see Pesu M, et al. JAK3, severe combined immunodeficiency, and a new class of immunosuppressive drugs. *Immunol Rev.* 203:127-42. 2005). CP-690-550, a pan Jak inhibitor, blocks the mixed lymphocyte reaction (MLR) (see Kudlacz E, et al. The novel JAK-3 inhibitor CP-690550 is a potent immunosuppressive agent in various murine models. *Am J Transplant.* 4:51-7. 2004), the delayed-type hypersensitivity response (DTH) (see Kudlacz E, et al. The novel JAK-3 inhibitor CP-690,550 is a potent immunosuppressive agent in various murine models. *Am J Transplant.* 4:51-7. 2004), as well as the collagen-induced arthritis model (see Milici A J, et al. Cartilage preservation by inhibition of Janus kinase 3 in two rodent models of rheumatoid arthritis. *Arthritis Res Ther.* 10:R14 1-9. 2008). Other Jak family members include Jak2, which is involved in hematopoietic growth factor signaling, and Jak1 and Tyk2 which in combination with Jak2 are important for interferon signaling and contribute to host resistance (see Shuai K and Liu B. Regulation of JAK-STAT signaling in the immune system. *Nat Rev Immunol.* 3:900-11. 2003).

Compounds that target the JAK pathway are in clinical development, but none is selective for a single JAK family member. However, these studies provide clinical validation of the JAK pathway in rheumatoid arthritis (see Krenmer J, et al. The oral Jak inhibitor CP-690,550 in combination with methotrexate is efficacious, safe and well tolerated in patients with active rheumatoid arthritis with an inadequate response to methotrexate alone. *Arthritis & Rheum.* 58:4030a. 2008). Improvements in disease activity are observed as early as 1 week after initiation of treatment with significant improvements in ACR20, ACR50 and ACR70 as early as 4 weeks. Other clinical applications for JAK3 inhibition include kidney transplantation, Crohn's disease, psoriasis, and JAK3-dependent hematopoietic malignancies (see Ghoreschi K, et al., Janus kinases in immune cell signaling. *Immunol Rev.* 228:273-87. 2009). A short-term study with CP-690,550 on psoriasis patients demonstrated efficacy, suggesting possible utility in this indication (see Boy M G, et al. Double-blind, placebo-controlled, dose-escalation study to evaluate the pharmacologic effect of CP-690,550 in patients with psoriasis. *J Invest Dermatol.* 129:2299-302. 2009).

In addition, mutations resulting in persistent activation of JAK/STAT signaling have been described and attributed to the pathogenesis of various leukemias and lymphomas including T-cell acute lymphoblastic leukemia (T-ALL; Bains, T. et al. Newly described activating JAK3 mutations in T-cell acute lymphoblastic leukemia. *Leukemia* 26: 2144-2146. 2012; Elliott, N. E. et al FERM domain mutations induce gain of function in JAK3 in adult T-cell leukemia/lymphoma. *Blood* 118: 3911-3921. 2011), and natural killer cell-T cell lymphoma (NK-TCL; Bouchekioua, A. et al., JAK3 deregulation by activating mutations confers invasive growth advantage in extranodal nasal-type natural killer cell lymphoma. *Leukemia* May 21.2013; Koo, G. C. et al. Janus kinase 3-activating mutations identified in natural killer/T-cell lymphoma. *Cancer Discovery* 2: 591-597, 2013). Studies in BaF3 cells have shown that these mutations can be transforming (Malinge, S. et al. Activating mutations in human acute megakaryoblastic leukemia. *Blood* 112: 4220-4226. 2008; Walters, D. K. et al Activating alleles of JAK3 in acute megakaryoblastic leukemia. *Cancer Cell* 10: 65-75, 2006). The JAK-STAT pathway may be also be activated in other T-cell lymphomas even though there are no detectable mutations in JAK3, resulting from loss of SHP1, SOCS3, NPM-ALK fusion or other unknown causes. For example, constitutive STAT5 activation is a characteristic feature of malignant cell lines derived from the skin and blood of CTCL patients (Fantin, V R et al. Constitutive activation of signal transducers and activators of transcription predicts vorinostat resistance in cutaneous T-cell lymphoma. *Cancer Res.* 68:3785-3794. 2008). The pan-JAK inhibitor CP-690, 550 inhibits proliferation of JAK3 mutated NK-TCL cells (Koo, G. C. et al. Janus kinase 3-activating mutations identified in natural killer/T-cell lymphoma. *Cancer Discovery* 2: 591-597, 2013).

Accordingly, there is a need for compounds that inhibit JAK3 thereby providing treatment for diseases such as autoimmune diseases, inflammatory diseases, and cancer.

SUMMARY

In one aspect, provided are a compound of Formula (I):

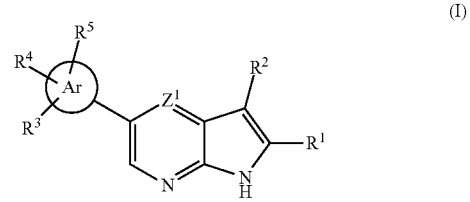

wherein:

$Z^1$ is N or $CR^6$ where $R^6$ is hydrogen, alkyl, halo, haloalkyl, haloalkoxy, or cyano;

$R^1$ is hydrogen, alkyl, halo, haloalkyl, haloalkoxy, cyano, or cycloalkyl;

$R^2$ is hydrogen, alkyl, cycloalkyl, halo, cyano, acyl, aminocarbonyl, phenyl or heteroaryl wherein phenyl and heteroaryl is optionally substituted with one, two or three substituents independently selected from alkyl, alkoxy, halo, haloalkyl, or haloalkoxy;

Ar is phenyl or 5- or 6-membered heteroaryl;

$R^3$ is -(alkylene)$_n$-Y—CH=CHR$^c$ [where n is 0 or 1, Y is —NR$^a$CO—, —NR$^a$SO$_2$—, —CO— or —SO$_2$— (where R$^a$ is hydrogen or alkyl) and R$^c$ is hydrogen, alkyl, NH$_2$alkyl, alkylaminoalkyl, or dialkylaminoalkyl] or -(alkylene)$_n$-Y—CH=CR$^d$ where R$^d$ is hydrogen or alkyl;

$R^4$ is hydrogen, alkyl, alkoxy, hydroxyl, halo, haloalkyl, haloalkoxy, hydroxyalkyl, hydroxyalkoxy, alkoxyalkyl, alkoxyalkyloxy, heterocyclylalkyl optionally substituted with one or two substitutents independently selected from alkyl, halo, hydroxyalkyl, or alkoxyalkyl, heterocyclyloxy optionally substituted with one or two substitutents independently selected from alkyl, halo, hydroxyalkyl, or alkoxyalkyl, heterocyclylalkyloxy optionally substituted with one or two substitutents independently selected from alkyl, halo, hydroxyalkyl, or alkoxyalkyl, aminoalkyl, or aminoalkoxy; and $R^5$ is hydrogen, alkyl, alkoxy, hydroxyl, halo, haloalkyl, haloalkoxy, or cyano; and/or a pharmaceutically acceptable salt thereof.

In one embodiment, the compounds of Formula (I) forms irreversible covalent bond with cysteine 909, (UniprotKB Sequence ID P52333) of JAK3.

In a second aspect, provided is a pharmaceutical composition comprising a compound of Formula (I) (or any of the embodiments thereof described herein), and/or a pharmaceutically acceptable salt thereof; and a pharmaceutically acceptable excipient.

In a third aspect, provided is a method of treating a disease treatable by inhibition of JAK3, in a patient which method comprises administering to the patient in need thereof, a pharmaceutical composition comprising a compound of Formula (I) (or any of the embodiments thereof described herein) or a pharmaceutically acceptable salt thereof and a pharmaceutically acceptable excipient in an amount effective to achieve the treatment (therapeutic amount). In one embodiment of the third aspect, the patient is in recognized need of such treatment.

In one embodiment of this aspect, the patient in need or recognized need is suffering from an autoimmune disease, e.g., inflammatory bowel disease, arthritis, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, Sjogren's syndrome, multiple sclerosis, Guillain-Barre syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, endometriosis, interstitial cystitis, neuromyotonia, scleroderma, or vulvodynia. In one embodiment of this aspect, the disease is rheumatoid arthritis. In another embodiment of this aspect, the autoimmune disease is lupus. In yet another embodiment of this aspect the autoimmune disease is psoriasis or transplant. In another embodiment of this aspect, the patient in need or recognized need is suffering from a heteroimmune condition or disease, e.g., graft versus host disease, transplantation, transfusion, anaphylaxis, allergy, type I hypersensitivity, allergic conjunctivitis, allergic rhinitis, or atopic dermatitis.

In another embodiment of this aspect, the patient in need or recognized need is suffering from an inflammatory disease, e.g., asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis.

In another embodiment of this aspect, the patient is in need or recognized need is suffering from inflammatory skin disease which includes, by way of example, dermatitis, contact dermatitis, eczema, urticaria, rosacea, and scarring psoriatic lesions in the skin, joints, or other tissues or organs.

In yet another embodiment of this aspect, the patient in need or recognized need is suffering from a cancer. In one embodiment the cancer is T-ALL, CTCL, NK-T cell lymphoma, Sezary syndrome, and Mycosis fungiodes. In some embodiments, the compound of Formula (I) (or any embodiments thereof described herein) and/or a pharmaceutically acceptable salt thereof is administered in combination with another an anti-cancer.

In a fourth aspect, provided are compounds of Formula (I) (and any embodiments thereof described herein) and/or a pharmaceutically acceptable salt thereof for use as a medicament. In one embodiment, the compounds of Formula (I) (and any embodiments thereof described herein) and/or a pharmaceutically acceptable salt thereof is for treating autoimmune diseases, inflammatory disease, or proliferative diseases such as cancer.

In a fifth aspect, provided is the use of a compound of Formula (I) (and any embodiments thereof described herein) and/or a pharmaceutically acceptable salt thereof in the manufacture of a medicament for treating a disease in a patient in which the activity of JAK3 contributes to the pathology and/or symptoms of the disease. In one embodiment of this aspect, the disease is autoimmune diseases, inflammatory disease, or proliferative diseases such as cancer.

In any of the aforementioned aspects involving the treatment of autoimmune diseases, inflammatory disease, or proliferative disorders, in one embodiment, the compounds of present disclosure are administered in combination with at least one other anti-autoimmune, anti-inflammatory, or antiproliferative agent. In one embodiment, the disease is cancer and the compound of Formula (I) (and any embodiments thereof described herein) is administered in combination with at least one additional anticancer agent such as alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzamab, methotrexate, paclitaxel, Taxol™, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, or dronabinol. When combination therapy is used, the agents can be administered simultaneously or sequentially.

DEFINITIONS

Unless otherwise stated, the following terms used in the specification and claims are defined for the purposes of this application and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), pentyl (including all isomeric forms), and the like.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"Alkylthio" means a —SR radical where R is alkyl as defined above, e.g., methylthio, ethylthio, and the like.

"Alkylsulfonyl" means a —SO$_2$R radical where R is alkyl as defined above, e.g., methylsulfonyl, ethylsulfonyl, and the like.

"Amino" means a —NH$_2$.

"Alkylamino" means an —NHR radical where R is alkyl as defined above, e.g., methylamino, ethylamino, propylamino, or 2-propylamino, and the like.

"Alkylaminoalkyl" means a linear monovalent hydrocarbon radical of one to six carbon atoms or a branched monovalent hydrocarbon radical of three to six carbons substituted with at least one —NHR group, (in one embodiment one —NHR group) where R is alkyl as defined above, e.g., 2-methyaminoethyl, 2-methyamino- or 3-methylaminopropyl, and the like.

"Dialkylaminoalkyl" means a linear monovalent hydrocarbon radical of one to six carbon atoms or a branched monovalent hydrocarbon radical of three to six carbons substituted with at least one —NRR' group, (in one embodiment one —NRR' group) where R and R' are alkyl as defined above, e.g., 2-dimethyaminoethyl, 2-dimethyamino- or 3-dimethylaminopropyl, and the like.

"Aminoalkyl" means a linear monovalent hydrocarbon radical of one to six carbon atoms or a branched monovalent hydrocarbon radical of three to six carbons substituted with at least one NRR' group, (in one embodiment one NRR' group) where R and R' are independently hydrogen or alkyl as defined above, e.g., 2-aminoethyl, 2-methyamino- or 2-dimethylaminoethyl, and the like.

"Aminoalkyloxy" a —OR radical where R is aminoalkyl as defined above, e.g., e.g., 2-aminoethyloxy, 2-methyamino- or 2-dimethylaminoethyloxy, diethylaminopropyloxy, and the like.

"Alkoxy" means a —OR radical where R is alkyl as defined above, e.g., methoxy, ethoxy, propoxy, or 2-propoxy, n-, iso-, or tert-butoxy, and the like.

"Alkoxyalkyl" means a linear monovalent hydrocarbon radical of one to six carbon atoms or a branched monovalent hydrocarbon radical of three to six carbons substituted with at least one alkoxy group, (in one embodiment one or two alkoxy groups), as defined above, e.g., 2-methoxyethyl, 1-, 2-, or 3-methoxypropyl, 2-ethoxyethyl, and the like.

"Alkoxyalkyloxy" means a —O-alkoxyalkyl radical where alkoxyalkyl is as defined above. Representative examples include, but are not limited to, methoxymethyloxy, 2-methoxyethyloxy, 2-methoxypropyloxy, 3-methoxypropyloxy, and the like.

"Alkylcarbonyl" means an —COR radical where R is alkyl as defined above. Representative examples include, but are not limited to, methylcarbonyl, and the like.

"Alkoxycarbonyl" means a —C(O)OR radical where R is alkyl as defined above, e.g., methoxycarbonyl, ethoxycarbonyl, and the like.

"Aminocarbonyl" means a —CONR"R' radical where R" is independently hydrogen, alkyl, or substituted alkyl, each as defined herein and R' is hydrogen, alkyl, cycloalkyl, cycloalkylalkyl, aryl, aralkyl, heteroaryl, heteroaralkyl, heterocyclyl, heterocyclylalkyl, or substituted alkyl, each as defined herein and wherein the cycloalkyl, aryl, heteroaryl or heterocyclyl ring either alone or part of another group such as aralkyl, is optionally substituted with one, two, or three substituents independently selected from alkyl, halo, haloalkyl, haloalkoxy, alkoxy, cyano, carboxy, hydroxyl, —CONR"R' (where R" and R' are hydrogen or alkyl) alkylcarbonyl, alkylthio, or alkylsulfonyl, e.g., —CONH$_2$, methylaminocarbonyl, 2-dimethylaminocarbonyl, and the like.

"Acyl" means a —COR radical where R is alkyl, substituted alkyl, haloalkyl, cycloalkyl, cycloalkylalkyl, aryl, aralkyl, heteroaryl, heteroaralkyl, heterocyclyl, or heterocyclylalkyl, each as defined herein and wherein the cycloalkyl, aryl, heteroaryl or heterocyclyl ring either alone or part of another group such as aralkyl, is optionally substituted with one, two, or three substituents independently selected from alkyl, halo, haloalkyl, haloalkoxy, alkoxy, cyano, carboxy, hydroxyl, —CONR"R' (where R" and R' are hydrogen or alkyl), alkylcarbonyl, alkylthio, or alkylsulfonyl, e.g., acetyl, propionyl, benzoyl, pyridinylcarbonyl, and the like. When R" is alkyl, the radical is also referred to herein as alkylcarbonyl.

"Aryl" means a monovalent monocyclic or bicyclic aromatic hydrocarbon radical of 6 to 10 ring atoms e.g., phenyl or naphthyl.

"Aralkyl" means a -(alkylene)-R radical where R is aryl as defined above.

"Cycloalkyl" means a cyclic saturated monovalent hydrocarbon radical of three to ten carbon atoms wherein one or two carbon atoms may be replaced by an oxo group, e.g., cyclopropyl, cyclobutyl, cyclopentyl, or cyclohexyl, and the like.

"Cycloalkylalkyl" means a -(alkylene)-R radical where R is cycloalkyl as defined above; e.g., cyclopropylmethyl, cyclobutylmethyl, cyclopentylethyl, or cyclohexylmethyl, and the like.

"Carboxy" means —COOH.

"Halo" means fluoro, chloro, bromo, or iodo. In one embodiment, halo is fluoro or chloro.

"Haloalkyl" means alkyl radical as defined above, which is substituted with one or more halogen atoms, (in one embodiment one to five halogen atoms), such as fluorine or chlorine, including those substituted with different halogens, e.g., —CH$_2$Cl, —CF$_3$, —CHF$_2$, —CH$_2$CF$_3$, —CF$_2$CF$_3$, —CF(CH$_3$)$_2$, and the like. When the alkyl is substituted with only fluoro, it is referred to in this Application as fluoroalkyl.

"Haloalkoxy" means a —OR radical where R is haloalkyl as defined above e.g., —OCF$_3$, —OCHF$_2$, and the like. When R is haloalkyl where the alkyl is substituted with only fluoro, it is referred to in this application as fluoroalkoxy.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl. In one embodiment hydroxyalkyl is 2-hydroxyethyl, 2,3-dihydroxypropyl, and 1-(hydroxymethyl)-2-hydroxyethyl.

"Hydroxyalkyloxy" means a —O-hydroxyalkyl radical where hydroalkyl is as defined above. Representative examples include, but are not limited to, hydroxymethyloxy, 2-hydroxyethyloxy, 2-hydroxypropyloxy, 3-hydroxypropyloxy, 1-(hydroxymethyl)-2-methylpropyloxy, 4-hydroxybutyloxy, and the like.

"Heterocyclyl" means a saturated or unsaturated monovalent monocyclic group of 4 to 8 ring atoms in which one or two ring atoms are heteroatom selected from N, O, or S(O)$_n$, where n is an integer from 0 to 2, the remaining ring atoms being C. The heterocyclyl ring is optionally fused to a (one) aryl or heteroaryl ring as defined herein provided the aryl and heteroaryl rings are monocyclic. The heterocyclyl ring fused to monocyclic aryl or heteroaryl ring is also referred to in this application as "bicyclic heterocyclyl" ring. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholino, piperazino, tetrahydropyranyl, oxetanyl, thiomorpholino, and the like. When the heterocyclyl ring is unsaturated it can contain one or two ring double bonds provided that the ring is not aromatic. When the heterocyclyl group contains at least one nitrogen atom, it is also referred to herein as heterocycloamino and is a subset of the heterocyclyl group. When the heterocyclyl group is a saturated ring and is not fused to aryl or heteroaryl ring as stated above, it is also referred to herein as saturated monocyclic heterocyclyl.

"Heterocyclyloxy" means a —O-heterocyclyl radical where heterocyclyl is as defined above. Representative examples include, but are not limited to, piperidinyloxy, piperazinyloxy, tetrahydrofuranyloxy, oxetanyloxy, morpholinyloxy, and the like.

"Heterocyclylalkyl" means a -(alkylene)-R radical where R is heterocyclyl ring as defined above e.g., tetrahydrofuranylmethyl, piperazinylmethyl, morpholinylethyl, and the like.

"Heterocyclylalkyloxy" means a —O-heterocyclylalkyl radical where heterocyclylalkyl is as defined above. Representative examples include, but are not limited to, piperidinylmethyloxy, piperazinylethyl- or propyloxy, tetrahydrofuranylmethyloxy, morpholinylmethyl-, ethyl-, or propyloxy, and the like.

"Heterocycloamino" means a saturated or unsaturated monovalent monocyclic group of 4 to 8 ring atoms in which one or two ring atoms are heteroatom selected from N, O, or S(O)$_n$, where n is an integer from 0 to 2, the remaining ring atoms being C provided that at least one of the ring atoms is N. Additionally, one or two ring carbon atoms in the heterocycloamino ring can optionally be replaced by a —CO— group. Unless otherwise stated, the heterocycloamino ring can optionally be substituted with one, two, or three substituents independently selected from alkyl, hydroxyl, alkoxy, amino, alkylamino, or dialkylamino.

"Heteroaryl" means a monovalent monocyclic or bicyclic aromatic radical of 5 to 10 ring atoms where one or more, (in one embodiment one, two, or three), ring atoms are heteroatom selected from N, O, or S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like.

"Heteroaralkyl" means an -alkylene-R radical where R is heteroaryl as defined above.

The present disclosure also includes the prodrugs of compounds of Formula (I). The term prodrug is intended to represent covalently bonded carriers, which are capable of releasing the active ingredient of Formula (I) when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups in vivo or by routine manipulation. Prodrugs of compounds of Formula (I) include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of Formula (I)), amides (e.g., trifluoroacetylamino, acetylamino, and the like), and the like. Prodrugs of compounds of Formula (I) are also within the scope of the present disclosure.

The present disclosure also includes protected derivatives of compounds of Formula (I). For example, when compounds of Formula (I) contain groups such as hydroxy, carboxy, thiol or any group containing a nitrogen atom(s), these groups can be protected with a suitable protecting groups. A comprehensive list of suitable protective groups can be found in T. W. Greene, *Protective Groups in Organic Synthesis*, John Wiley & Sons, Inc. (1999), the disclosure of which is incorporated herein by reference in its entirety. The protected derivatives of compounds of Formula (I) can be prepared by methods well known in the art.

The present disclosure also includes polymorphic forms (amorphous as well as crystalline) and deuterated forms of compounds of Formula (I).

A "pharmaceutically acceptable salt" of a compound means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences*, 17th ed., Mack Publishing Company, Easton, Pa., 1985, which is incorporated herein by reference.

The compounds of the present disclosure may have asymmetric centers. Compounds of the present disclosure containing an asymmetrically substituted atom may be isolated in optically active or racemic forms. It is well known in the art how to prepare optically active forms, such as by resolution of materials. All chiral, diastereomeric, racemic forms are within the scope of the present disclosure, unless the specific stereochemistry or isomeric form is specifically indicated.

Certain compounds of Formula (I) can exist as tautomers and/or geometric isomers. All possible tautomers and cis and trans isomers, as individual forms and mixtures thereof are within the scope of this disclosure. Additionally, as used herein the term alkyl includes all the possible isomeric forms of said alkyl group albeit only a few examples are set forth. Furthermore, when the cyclic groups such as aryl, heteroaryl, heterocyclyl are substituted, they include all the positional isomers albeit only a few examples are set forth. Furthermore, all polymorphic forms and hydrates of a compound of Formula (I) are within the scope of this disclosure.

"Oxo" or "carbonyl" means =(O) group.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes situations where the heterocyclyl group is substituted with an alkyl group and situations where the heterocyclyl group is not substituted with alkyl.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

"Substituted alkyl" means alkyl group as defined herein which is substituted with one, two, or three substituents independently selected from hydroxyl, alkoxy, carboxy, cyano, alkoxycarbonyl, alkylthio, alkylsulfonyl, halo, haloalkoxy, —SO$_2$NRR', —CONR"R' or —NRR' (where each R or R" is hydrogen, alkyl, hydroxyalkyl, or alkoxyalkyl, and each R' is hydrogen, alkyl, or cycloalkyl) or heterocyclyl (in one embodiment heterocycloamino) optionally substituted with one or two groups independently selected from alkyl, hydroxyl, alkoxy, alkylthio, alkylsulfonyl, halo, or —CONR"R' (where R, R', and R" are independently hydrogen or alkyl).

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease;

(2) inhibiting the disease, i.e., arresting or reducing the development of the disease or its clinical symptoms; or (3) relieving the disease, i.e., causing regression of the disease or its clinical symptoms.

A "therapeutically effective amount" means the amount of a compound of Formula (I) that, when administered to a patient for treating a disease, is sufficient to effect such treatment for the disease. The "therapeutically effective amount" will vary depending on the compound, the disease and its severity and the age, weight, etc., of the mammal to be treated.

Representative compounds of Formula (I) are shown in Compound Table I below:

TABLE 1

| CPD # | Name |
|---|---|
| 1 | N-(3-(7-pivaloyl-5H-pyrrolo[2,3-b]pyrazin-2-yl)phenyl)acrylamide |
| 2 | 2-(3-acrylamidophenyl)-N-(tert-butyl)-5H-pyrrolo[2,3-b]pyrazine-7-carboxamide |
| 3 | N-(tert-butyl)-2-(3-(4-(dimethylamino)but-2-enamido)phenyl)-5H-pyrrolo[2,3-b]pyrazine-7-carboxamide | or a mixture of E and Z isomers; or a pharmaceutically acceptable salt thereof.

EMBODIMENTS

Embodiment A

In one group of compounds, the compound of Formula (I) or salt thereof has the structure (Ia):

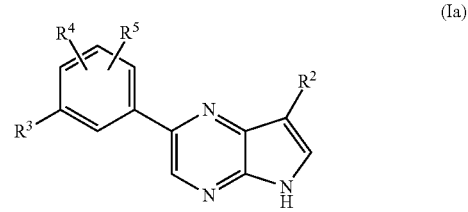

(Ia)

where the variables $R^2$, $R^3$, $R^4$, and $R^5$ have the same definitions as those in Formula I.

(i) Within compounds or salt thereof in embodiment A, in one group of compounds or salt thereof, the compounds have structure (Ib):

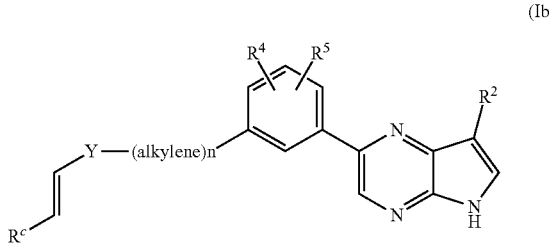

(Ib)

where the variables $R^2$, $R^4$, $R^5$, $R^c$, Y, and n have the same definitions as those in Formula I.

Embodiment B

In other embodiments of Formula (I) Ar is 5- or 6-membered heteroaryl.

Within embodiment B, in one group of compounds or salt thereof Ar is pyridinyl, pyridazinyl, pyrazinyl, or pyrimidinyl, each ring substituted with $R^3$, where $R^3$ is -(alkylene)$_n$-Y—CH=CHR$^c$, on the carbon atom of the ring that is at the meta position to the carbon attaching the aforementioned rings to the azaindole core.

Embodiment C

The compound of Formula (I) or salt thereof as defined in the Summary, embodiments A and B, and groups contained therein, wherein $R^2$ is hydrogen, alkyl, cycloalkyl, halo, cyano, —COR (where R is alkyl, heterocyclyl, heterocyclylalkyl or substituted alkyl), or —CONR"R' (where R" is hydrogen or alkyl and R' is hydrogen, alkyl, heterocyclyl, heterocyclylalkyl, or substituted alkyl).

Embodiment D

The compound of Formula (I) or salt thereof as defined in the Summary, embodiments A and B, and groups contained therein, wherein $R^2$ is hydrogen, methyl, isopropyl, tert-butyl, cyclopropyl, fluoro or cyano. Within the groups in Embodiment D, in one group of compounds, $R^2$ is hydrogen, methyl, tert-butyl, cyclopropyl, fluoro or cyano.

Embodiment E

The compound of Formula (I) or salt thereof as defined in the Summary, embodiments A and B, and groups contained therein, wherein $R^2$ is acyl. Within the groups in Embodiment E, in one group of compounds $R^2$ is —COR where R is alkyl. Within the groups in Embodiment E, in another group of compounds $R^2$ is —COR where R is isopropyl, isobutyl, or tert-butyl. Within the groups in Embodiment E, in yet another group of compounds $R^2$ is —COR where R is tert-butyl.

Embodiment F

The compound of Formula (I) or salt thereof as defined in the Summary, embodiments A and B, and groups contained therein, wherein $R^2$ is —COR where R is cycloalkyl or heterocyclyl. Within the groups in Embodiment F, in one group of compounds $R^2$ is —COR where R is cyclopropyl, cyclohexyl, cyclopentyl, pyrrolidinyl, tetrahydropyranyl, piperidinyl, tetrahydrothiopyranyl, or 1,1,-dioxo-tetrahydrothiopyranyl. In one embodiment R is cyclopropyl, 3-, or 4-pyrrolidinyl, 3- or 4-tetrahydropyranyl, 3- or 4-piperidinyl, 3- or 4-tetrahydrothiopyranyl, 3- or 4-1,1,-dioxo-tetrahydrothiopyranyl, each of which is optionally substituted at the carbon attached to —CO— with alkyl. Within the groups in Embodiment F, in another group of compounds $R^2$ is —COR where methyl and the ring with a ring nitrogen atoms is optionally substituted at ring nitrogen with alkylcarbonyl. Within the groups in Embodiment F, in one group of compounds $R^2$ is where acetyl. Within the groups in Embodiment F, in one group of compounds $R^2$ is —COR where R is 1-methylcyclohex-1-yl.

Embodiment G

The compound of Formula (I) or salt thereof as defined in the Summary, embodiments A and B, and groups contained therein, wherein $R^2$ is —COR where R is heterocyclylalkyl. Within the groups in Embodiment G, in one group of compounds $R^2$ is —COR where R is heterocyclyl ring is pyrrolidinyl, tetrahydropyranyl, piperidinyl, tetrahydrothiopyranyl, or 1,1,-dioxo-tetrahydrothiopyranyl. Within the groups in Embodiment G, in another group of compounds $R^2$ is —COCH$_2$heterocyclyl where the heterocyclyl ring is 3-, or 4-pyrrolidinyl, 3- or 4-tetrahydropyranyl, 3- or 4-piperidinyl, 3- or 4-tetrahydrothiopyranyl, 3- or 4-1,1,-dioxo-tetrahydrothiopyranyl, each ring containing nitrogen ring atom is optionally substituted at ring nitrogen with alkylcarbonyl such as acetyl and each ring is optionally substituted at the carbon attached to —CR$_2$— with alkyl, such as methyl.

Embodiment H

The compound of Formula (I) or salt thereof as defined in the Summary, embodiments A and B, and groups contained therein, wherein $R^2$ is —COR where R is substituted alkyl. Within the groups in Embodiment H, in one group of compounds $R^2$ is —COR where R is alkyl substituted with one or two hydroxyl, alkoxy, or amino. Within the groups in Embodiment H, in another group of compounds $R^2$ is —COR where R is 1,3-dimethoxyprop-2-yl, —C(CH$_3$)$_2$CH$_2$NH$_2$, —CH(CH$_3$)CH$_2$OCH$_3$, 1,3-dihydroxyprop-2-yl, —CH(CH$_3$)CH$_2$OH, 1,3-dihydroxy-2-methylprop-2-yl, —C(CH$_3$)(OC$_2$H$_5$)$_2$, —CH$_2$C(CH$_3$)$_2$CH$_2$OH, 2-hydroxypropyl, 3-methoxyprop-2-yl, 2-methoxyprop-1-yl, 2,3-dihydroxyprop-1-yl, 2-methoxyethyl, 3-methoxypropyl, —CH$_2$C(CH$_3$)$_2$OCH$_3$, 3-methoxybutyl, —C(CH$_3$)$_2$OCH$_3$, or methoxymethyl.

Embodiment I

The compound of Formula (I) or salt thereof as defined in the Summary, embodiments A and B, and groups contained therein, wherein $R^2$ is aminocarbonyl. Within the groups in Embodiment I, in one group of compounds $R^2$ is —CONHR' where R' is alkyl. Within the groups in Embodiment I, in one group of compounds $R^2$ is —CONHR' where R' is isopropyl, isobutyl, or tert-butyl. Within the groups in Embodiment I, in one group of compounds $R^2$ is —NH tert-butyl. Within the groups in Embodiment I, in one group of compounds $R^2$ is —CONHisopropyl.

Embodiment J

The compound of Formula (I) or salt thereof as defined in the Summary, embodiments A and B, and groups contained therein, wherein $R^2$ is —CONHR' where R' is cycloalkyl or heterocyclyl. Within the groups in Embodiment J, in one group of compounds $R^2$ is —CONHR' where R' is cyclopropyl, cyclohexyl, cyclopentyl, pyrrolidinyl, tetrahydropyranyl, piperidinyl, tetrahydrothiopyranyl, or 1,1,-dioxo-tetrahydrothiopyranyl (in one embodiment cyclopropyl, 3-, or 4-pyrrolidinyl, 3- or 4-tetrahydropyranyl, 3- or 4-piperidinyl, 3- or 4-tetrahydrothiopyranyl, 3- or 4-1,1,-dioxo-tetrahydrothiopyranyl), each of which is optionally substituted at the carbon attached to —NH— with alkyl (in one embodimentmethyl) and ring containing nitrogen ring atom is optionally substituted at ring nitrogen with alkylcarbonyl (in one embodiment acetyl). Within the groups in Embodiment J, in one group of compounds $R^2$ is —CONH 1-methylcyclohex-1-yl.

Embodiment K

The compound of Formula (I) or salt thereof as defined in the Summary, embodiments A and B, and groups contained therein, wherein $R^2$ is —CONHR' where R' is heterocyclylalkyl. Within the groups in Embodiment K, in one group of compounds $R^2$ is —CONHR' where R' is heterocyclylalkyl where heterocyclyl ring is pyrrolidinyl, tetrahydropyranyl, piperidinyl, tetrahydrothiopyranyl, or 1,1,-dioxo-tetrahydrothiopyranyl. Within the groups in Embodiment K, in another group of compounds $R^2$ is —COCH$_2$-heterocyclyl where heterocyclyl is 3-, or 4-pyrrolidinyl, 3- or 4-tetrahydropyranyl, 3- or 4-piperidinyl, 3- or 4-tetrahydrothiopyranyl, or 3- or 4-1,1,-dioxo-tetrahydrothiopyranyl, each ring containing nitrogen ring atom is optionally substituted at ring nitrogen with alkylcarbonyl (in one embodiment acetyl) and each ring is optionally substituted at the carbon attached to —CH$_2$— with alkyl (in one embodiment methyl).

Embodiment L

The compound of Formula (I) or salt thereof as defined in the Summary, embodiments A and B, and groups contained therein, wherein $R^2$ is —CONHR' where R' is substituted alkyl. Within the groups in Embodiment L, in one group of compounds $R^2$ is —CONHR' where R' is alkyl substituted with one or two hydroxyl, alkoxy, amino. Within the groups in Embodiment L, in another group of compounds $R^2$ is —CONHR' where R' is 1,3-dimethoxyprop-2-yl, —C(CH$_3$)$_2$CH$_2$NH$_2$, —CH(CH$_3$)CH$_2$OCH$_3$, 1,3-dihydroxyprop-2-yl, —CH(CH$_3$)CH$_2$OH, 1,3-dihydroxy-2-methylprop-2-yl, —C(CH$_3$)(OC$_2$H$_5$)$_2$, —CH$_2$C(CH$_3$)$_2$CH$_2$OH, 2-hydroxypropyl, 3-methoxyprop-2-yl, 2-methoxyprop-1-yl, 2,3-dihydroxyprop-1-yl, 2-methoxyethyl, 3-methoxypropyl, —CH$_2$C(CH$_3$)$_2$OCH$_3$, 3-methoxybutyl, —C(CH$_3$)$_2$OCH$_3$, or methoxymethyl.

Embodiment M

The compound of Formula (I) or salt thereof as defined in the Summary, embodiments A-L, and groups contained therein, wherein $R^5$ is hydrogen, methyl, methoxy, fluoro, chloro, trifluoromethyl, cyano or trifluoromethoxy. Within the groups in Embodiment M, in one group of compounds $R^5$ is hydrogen.

Embodiment N

The compound of Formula (I) or salt thereof as defined in the Summary, embodiments A-M, and groups contained therein, wherein $R^4$ is hydrogen, alkyl, alkoxy, hydroxyl, halo, haloalkyl, haloalkoxy, hydroxyalkyl, hydroxyalkoxy, alkoxyalkyl, alkoxyalkyloxy, heterocyclylalkyl optionally substituted with one or two substitutents independently selected from alkyl, halo, hydroxyalkyl, or alkoxyalkyl, heterocyclyloxy optionally substituted with one or two substitutents independently selected from alkyl, halo, hydroxyalkyl, or alkoxyalkyl, heterocyclylalkyloxy optionally substituted with one or two substitutents independently selected from alkyl, halo, hydroxyalkyl, or alkoxyalkyl, aminoalkyl, or aminoalkoxy.

(i) Within the groups in embodiment N, in one group of compounds $R^4$ is hydrogen, alkyl, alkoxy, hydroxyl, halo, haloalkyl, or haloalkoxy. Within (i), in one group of compounds $R^4$ is hydrogen, methyl, methoxy, fluoro, chloro, trifluoromethyl, cyano or trifluoromethoxy.

(ii) Within the groups in embodiment N, in one group of compounds $R^4$ is hydroxyalkyl, hydroxyalkoxy, alkoxyalkyl, alkoxyalkyloxy, heterocyclylalkyl optionally substituted with one or two substitutents independently selected from alkyl, halo, hydroxyalkyl, or alkoxyalkyl, heterocyclyloxy optionally substituted with one or two substitutents independently selected from alkyl, halo, hydroxyalkyl, or alkoxyalkyl, heterocyclylalkyloxy optionally substituted with one or two substitutents independently selected from alkyl, halo, hydroxyalkyl, or alkoxyalkyl, aminoalkyl, or aminoalkoxy. Within (ii), in one group of compounds $R^4$ is hydroxyalkoxy, alkoxyalkyloxy, heterocyclyloxy optionally substituted with one or two substitutents independently selected from alkyl, halo, hydroxyalkyl, or alkoxyalkyl, heterocyclylalkyloxy optionally substituted with one or two substitutents independently selected from alkyl, halo, hydroxyalkyl, or alkoxyalkyl, or aminoalkoxy.

(iii) Within the groups in embodiment N, and subparts (i) and (ii), in one group of compounds $R^4$ is attached to carbon meta to carbon substituted with $R^3$ group.

Embodiment O (i) The compound of Formula (I) or salt thereof as defined in the Summary, embodiments A-N, and groups contained therein, wherein n is 1. Within these groups of compounds, in one group of compounds alkylene is methylene.

(ii) The compound of Formula (I) or salt thereof as defined in the Summary, embodiments A-N, and groups contained therein, wherein n is 0.

Embodiment P

The compound of Formula (I) or salt thereof as defined in the Summary, embodiments A-O, and groups contained therein, wherein Y is —NHCO—.

The compound of Formula (I) or salt thereof as defined in the Summary, embodiments A-O, and groups contained therein, wherein Y is —NHSO$_2$—.

The compound of Formula (I) or salt thereof as defined in the Summary, embodiments A-O, and groups contained therein, wherein Y is —CO—.

Embodiment Q

The compound of Formula (I) or salt thereof as defined in the Summary, embodiments A-P, and groups contained therein, wherein $R^c$ is hydrogen.

The compound of Formula (I) or salt thereof as defined in the Summary, embodiments A-P, and groups contained therein, wherein $R^c$ is methyl.

The compound of Formula (I) or salt thereof as defined in the Summary, embodiments A-P, and groups contained therein, wherein $R^c$ is NH$_2$alkyl, alkylaminoalkyl, or dialkylaminoalkyl. In one embodiment, $R^c$ is —CH$_2$NH$_2$, —CH$_2$NHCH$_3$, or —CH$_2$N(CH$_3$)$_2$ Compounds of the present disclosure can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of the present disclosure can be synthesized, and various modifications to these schemes can be made and will be suggested to one skilled in the art having referred to this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., such as from about 0° C. to about 125° C., or such as at about room (or ambient) temperature, e.g., about 20° C.

Compounds of this disclosure can be made by the methods depicted in the reaction schemes shown below.

Scheme 1 depicts the preparation of compounds of Formula (I) where $R^3$ is —Y—CH=$CHR^c$ or —Y—C(O)C≡$CR^d$ and Y is —$NR^a$CO— or —$NR^a$SO$_2$ where $R^a$, $R^c$, $R^d$, $R^1$—$R^5$ are as defined in the Summary.

Scheme 1

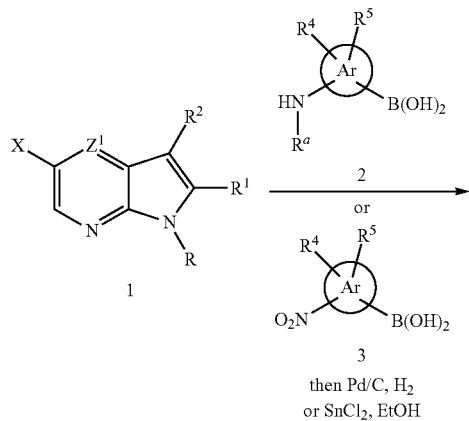

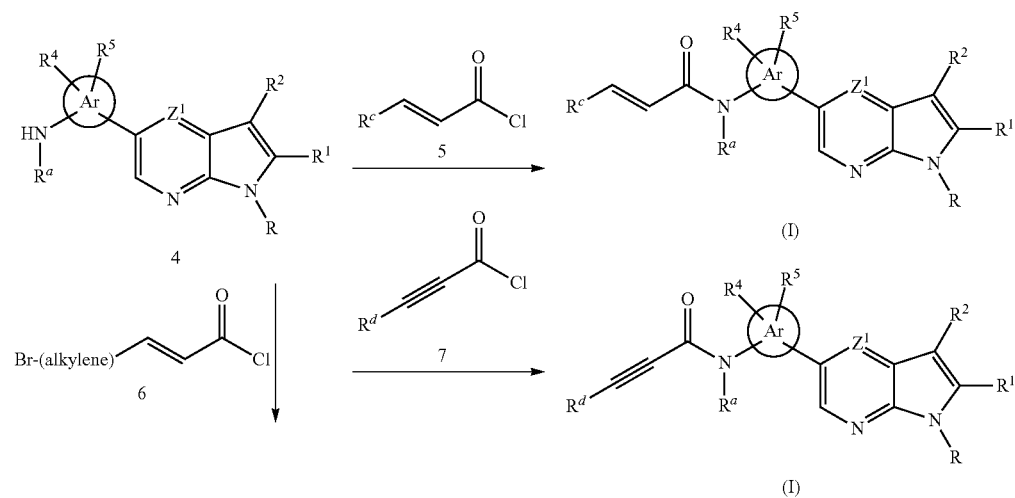

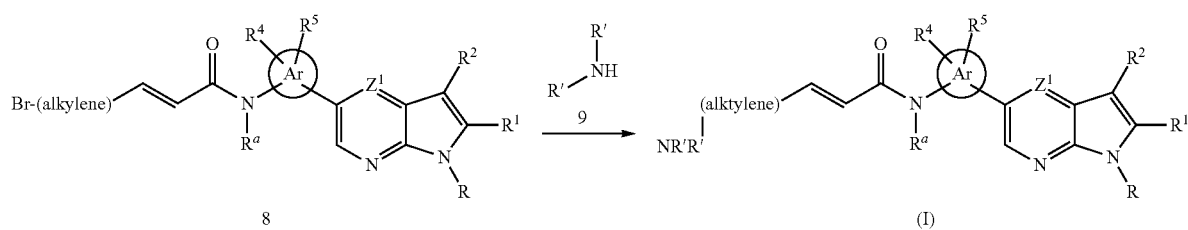

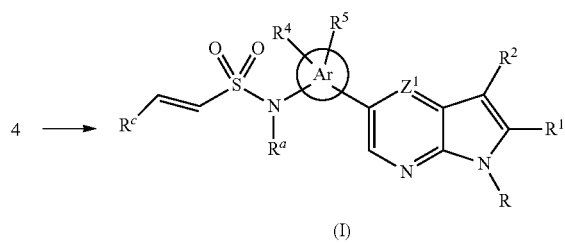

Reaction of a compound of formula 1 where R is H or a nitrogen protecting group such as SEM or TES, with a boronic acid compound of formula 2 where Ar, $R^a$, $R^4$ and $R^5$ are as defined in the Summary, under Suzuki-Miyaura coupling reaction conditions provides a compound of formula 4. The reaction is carried out in the presence of a catalyst such as Pd(PPh$_3$)$_4$ or PdCl(dppf)$_2$ and the like in a solvent mixture such as dioxane and water or dimethoxyethane and water. Alternatively, compound 1 can be reacted under the Suzuki-Miyaura coupling with a nitroaromatic boronic acid 3 and the nitro group subsequently reduced via the action of Pd/C and hydrogen or with SnCl$_2$ in a solvent such as MeOH to afford compound 4. Compounds of formula 1, 2 and 3 are either commercially available or they can be prepared by methods well known in the art. For example, a compound of formula 1, where X=Cl or Br, R=H or a PG such as SEM or TES and the like, $R^2$ is aminocarbonyl or acyl, and $R^1$ and $Z^1$ are defined in the Summary, can be prepared as shown in Methods (a), (b), or (c) below.

Method (a)

A compound of formula 1, where X=Cl or Br, R=H or a PG such as SEM or TES and the like, $R^2$ is aminocarbonyl and $R^1$ and $Z^1$ are defined in the Summary, can be prepared as shown in Methods (a), (b), or (c) below.

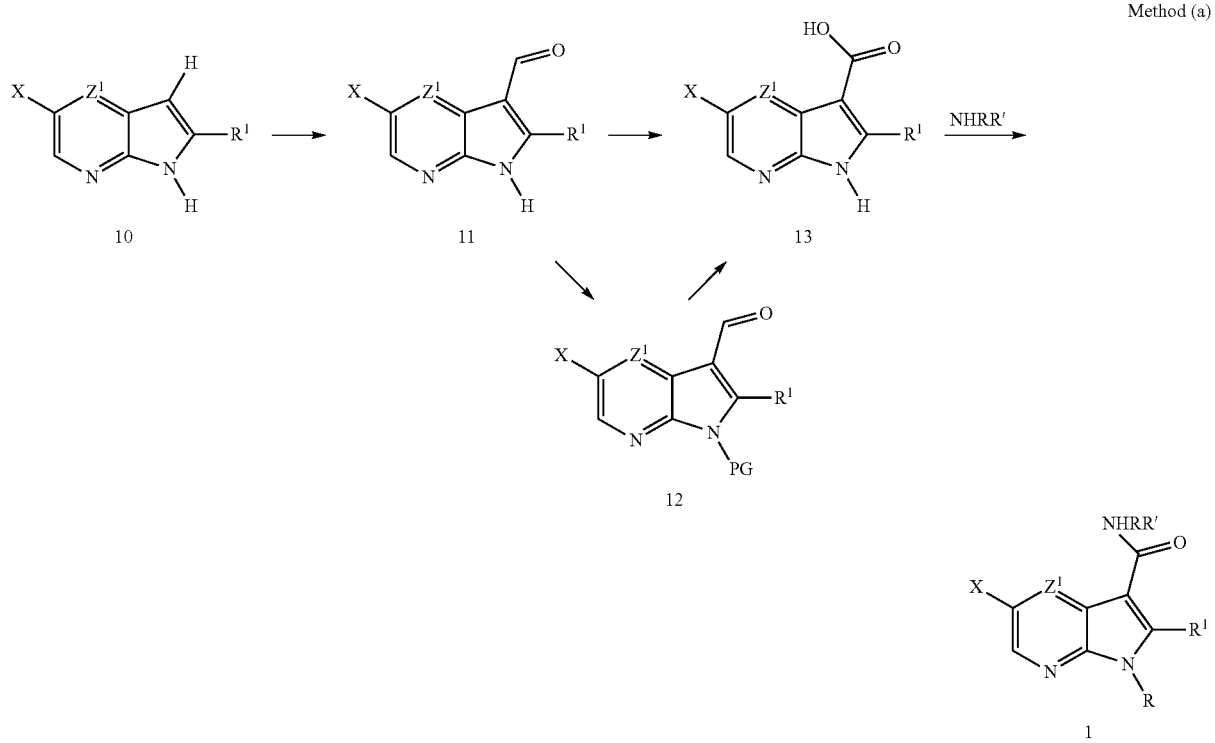

Formylation of a compound of formula 10 to give a compound of formula 11 can be accomplished by heating 10 in hexamethylenetriamine in trifluoroacetic acid as described in US patent application publication no. US2009/0215750A1. Compounds of formula 10 such as 2-bromo-5H-pyrrolo[2,3-b]pyrazine and 5-bromo-1H-pyrrolo[2,3-b]pyridine are commercially available. A compound of formula 12 where R is a nitrogen protecting group can be prepared by treating 11 with NaH in a solvent such as DMF followed by addition of SEMCl or other silyl protecting group such as TESCl. Treatment of compound 11 or 12 with a suitable oxidizing agent such as KH$_2$PO$_4$, NaClO$_2$ and sulfamic acid in dioxane and water provides a 3-carboxy compound of formula 13 where R is H or nitrogen protecting group. Subsequent amide coupling with a commercially available amine of formula NHRR' where R and R' are groups in the definition of aminocarbonyl using a suitable coupling reagents such as EDCI, DCC, and the like, and a base such as DMAP, diisopropylethylamine, and the like affords compounds of formula 1 where X=Cl or Br, R=H or a PG such as SEM or TES and the like, and $R^2$ is aminocarbonyl and R', and $Z^1$ are defined in the Summary.

A compound of formula 1, where X=Cl or Br, R=H or a PG such as SEM or TES and the like, $R^2$ is acyl, and $R^1$ and $Z^1$ are defined in the Summary, can be prepared as shown in Methods (b) or (c) below.

Method (b)

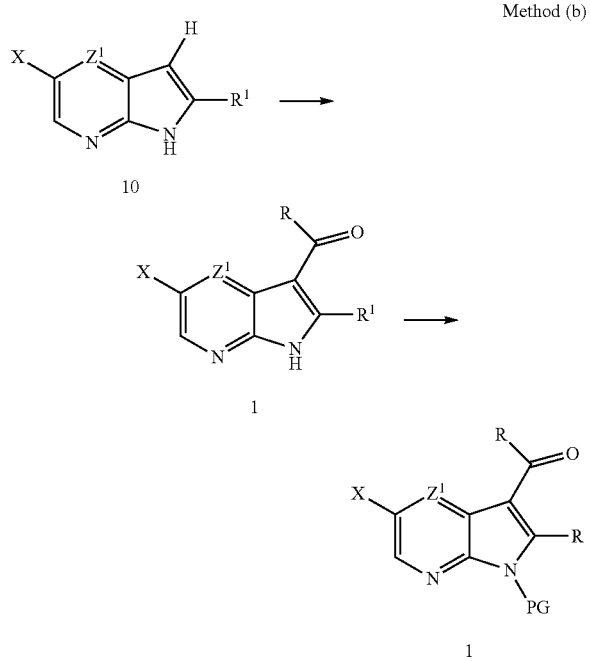

A compound of formula 10 can be treated with diethylaluminum chloride and an acid chloride of formula RC(O)Cl where is a group in the definition of acyl in a solvent such as dichloromethane, and the like to afford a ketone of formula 1. Incorporation of the protecting group such as SEM or TES can be accomplished as described in Method (a) to afford a compound of formula 1 where PG is protecting group.

Method (c)

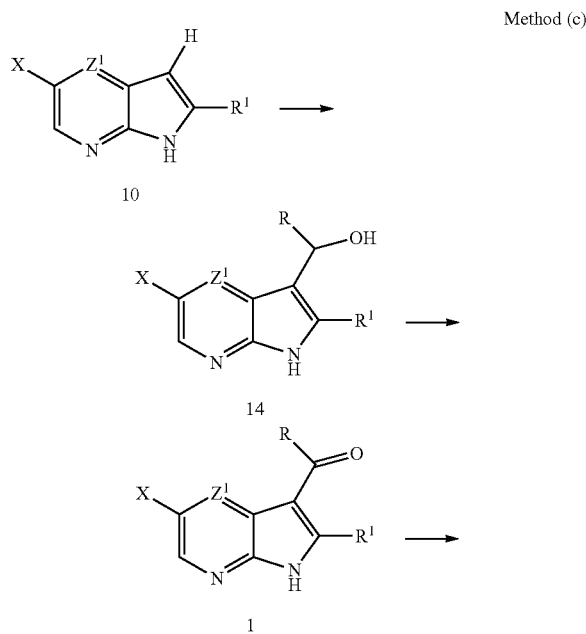

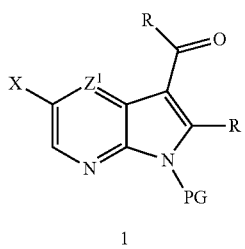

Alternatively, a compound of formula 10 can be treated with KOH and an aldehyde of formula RCHO where R is a group in the definition of acyl to afford a substituted alcohol of formula 14. Oxidation with, for example, Dess-Martin Periodinane in a solvent such as dichloromethane and the like affords a compound of formula 1 where R is hydrogen which can be protected as described in Method (a) to afford a compound of formula 1 where PG is a nitrogen protecting group.

Compounds of formula 4 can be converted to compounds of Formula (I) as described below. Compounds of Formula (I) where $R^3$ is —$NR^aCO$—CH=$CHR^c$ where $R^a$ and $R^c$ are as defined in the Summary can be prepared by acylation compound 4 with an acid chloride such as acryloyl chloride of formula 5 in the presence of a base such as triethylamine. Compounds of Formula (I) where $R^3$ is —Y—C(O)C≡$CR^d$ where $R^a$ and $R^d$ are as defined in the Summary can be prepared by acylation compound 4 with a propynyl chloride of formula 7 in the presence of a base such as triethylamine. Compounds of Formula (I) where $R^3$ is —$NR^aCO$—CH=$CHR^c$ where $R^c$ aminomethyl, alkylaminomethyl, or dialkylaminoalkyl and $R^c$ are as defined in the Summary can be prepared by coupling 4 with an acid chloride of formula 6 under amino acid coupling conditions to give a compound of formula 8 and further reaction with an amine of formula NHR'R' where each R' is independently hydrogen or alkyl. The nitrogen protected derivative of the compounds of Formula (I) can then be converted to corresponding compounds of Formula (I) by removal of the nitrogen protecting group. When the nitrogen protecting group is SEM or TES, it can be removed with an acid such as trifluoroacetic acid in a solvent such as dichloromethane followed by treatment with NaOAc in EtOH.

Proceeding as described above but substituting acyl halide with sulfonyl halide provides compounds of Formula (I) where Y is —$NR^aSO_2$—.

Compounds of Formula (I) where $R^3$ is -(alkylene)-Y—CH=$CHR^c$ where Y is —$NR^aCO$— or —$NR^aSO_2$ where $R^a$, $R^c$, $R^d$, and $R^1$—$R^5$ are as defined in the Summary can be prepared as illustrated and described in Scheme 2 below.

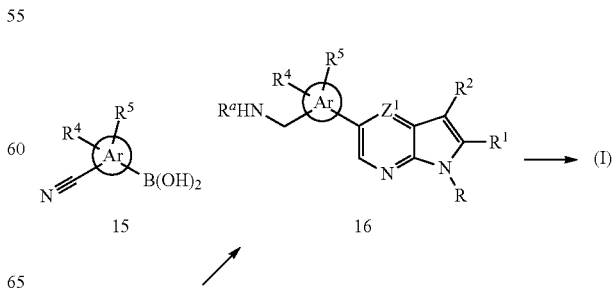

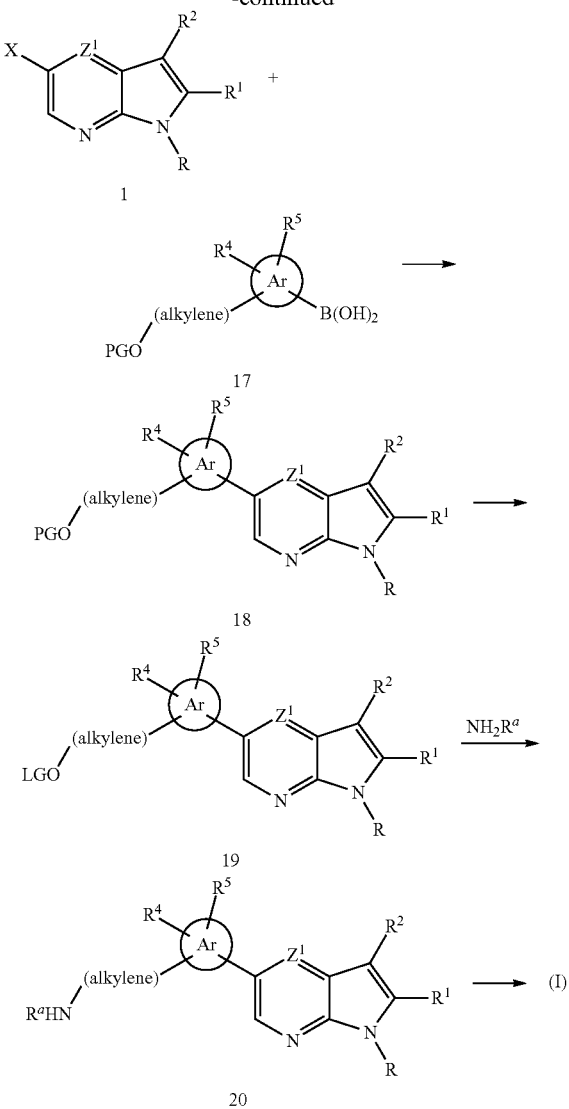

Compounds of formula 17 can be prepared in two steps from commercially available alcohols such as 2-(4-bromophenyl)ethanol, 2-(3-bromophenyl)ethanol, 2-(6-bromopyridin-3-yl)ethanol, 2-(5-bromopyridin-2-yl)ethanol, 4-bromobenzylalcohol, 4-bromobenzylalcohol, 3-(3-bromophenyl)propan-1-ol, 4-bromobenzenepropanol, 5-bromo-2-hydroxymethylpyridine, (2-Bromo-pyridin-5-yl)-methanol and the like. Protection of the alcohol moiety as a TBS ether or other silyl protecting groups is accomplished through methods well known in the art. Lithiation of the resulting aryl halide with a butyl lithium in a solvent such as THF followed by addition of trimethylborate affords compound 17 (i.e PCT2007076431).

The JAK3 inhibitory activity of the compounds can be measured utilizing the Biological assays 1-5 and 8 below. A determination of JAK3 inhibitory activity by any of those assays is considered to be JAK3 inhibitory activity within the scope of this disclosure even if any or all of the other assays do not result in a determination of kinase inhibitory activity.

The compounds of the present disclosure can form an irreversible covalent bond to Cys 909 (UniprotKB Sequence ID P52333) of JAK3. An irreversible covalent bond often imparts unique properties related to the residence time of the compound within the cysteine-containing binding site. In this context, residence time refers to the temporal duration of the compound-target complex under different conditions (see* Copeland R A, Pompliano D L, Meek T D. Drug-target residence time and its implications for lead optimization. Nat. Rev. Drug Discov. 5(9), 730-739 (2006). The presence of a irreversible covalent bond can lead to an extended residence time when compared to a non-covalent compound. Residence time may be measured using an occupancy assay in a biochemical or cellular environment. Additionally, residence time may be measured using a functional assay following a defined wash-out period. The ability of the compound of the disclosure to form irreversible covalent bond with Cys909 of JAK3 and the olefinic bond of -(alkylene)$_n$-Y—CH=CHR$^c$ group in the compound of the disclosure, can be determined by the assays described in Biological Examples 6 and 7 below. A determination of the binding irreversibility of the covalent bond between the cysteine residue and the olefinic bond of the compound of the disclosure by any of Biological Examples 6-7 below is considered to be binding irreversibility within the scope of this disclosure even if one of the other methods does not result in a determination of binding irreversibility.

Compounds of Formula (I) where R$^3$ is —(CH$_2$)—Y—CH=CHR$^c$ where Y is —NR$^a$CO— or —NR$^a$SO$_2$ where R$^a$, R$^c$, R$^d$, and R$^1$—R$^5$ are as defined in the Summary can be prepared by reacting a compound of formula 1 with a compound of formula 15, followed by reduction of the cyano group with a suitable reducing agent such as Pd/C to give a compound of formula 16. Compound 16 is then converted to a compound of Formula (I) as described in Scheme 1 above.

Compounds of Formula (I) where R$^3$ is -(alkylene)-Y—CH=CHR$^c$ where Y is —NR$^a$CO— or —NR$^a$SO$_2$ where R$^a$, R$^c$, R$^d$, and R$^1$—R$^5$ are as defined in the Summary can be prepared by reacting a compound of formula 1 with a boronic acid compound of formula 17 where PG is a suitable hydroxy protecting group to give a compound of formula 18. Removal of the hydroxyl protecting group followed by conversion of the resulting hydroxyl group to a suitable leaving group such as mesylate, tosylate, and the like provides a compound of formula 19. Compound 19 is then converted to a compound of formula 20 by treating 19 with an amine of formula NH$_2$R$^a$ where R$^a$ is as defined in the Summary. Compound 20 is then converted to a compound of Formula (I) as described in Scheme 1 above.

In general, the compounds of the present disclosure will be administered in a therapeutically effective amount by any of the accepted modes of administration for agents that serve similar utilities. Therapeutically effective amounts of compounds of the present disclosure may range from about 0.01 to about 500 mg per kg patient body weight per day, which can be administered in single or multiple doses. The dosage level can be about 0.1 to about 250 mg/kg per day; about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions can be in the form of tablets containing about 1.0 to about 1000 milligrams of the active ingredient, particularly about 1, 5, 10, 15, 20, 25, 50, 75, 100, 150, 200, 250, 300, 400, 500, 600, 750, 800, 900, and 1000 milligrams of the active ingredient. The actual amount of the compounds of the present disclosure, i.e., the active ingredient, will depend upon numerous factors such as the severity of the disease to be treated, the age and relative health of the subject, the potency of the compound being utilized, the route and form of administration, and other factors.

In general, compounds of the present disclosure will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules including enteric coated or delayed release tablets or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of the present disclosure in combination with at least one pharmaceutically acceptable excipient. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this disclosure in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 20th ed., 2000).

The level of the compound in a formulation can vary within the full range employed by those skilled in the art. Typically, the formulation will contain, on a weight percent (wt %) basis, from about 0.01-99.99 wt % of a compound of formula (I) based on the total formulation, with the balance being one or more suitable pharmaceutical excipients. For example, the compound is present at a level of about 1-80 wt %.

The compounds of the present disclosure may be used in combination with one or more other drugs in the treatment of diseases or conditions for which compounds of the present disclosure or the other drugs may have utility, where the combination of the drugs together are safer or more effective than either drug alone. Such other drug(s) may be administered, by a route and in an amount commonly used therefore, contemporaneously or sequentially with a compound of the present disclosure. When a compound of the present disclosure is used contemporaneously with one or more other drugs, a pharmaceutical composition in unit dosage form containing such other drugs and the compound of the present disclosure is preferred. However, the combination therapy may also include therapies in which the compound of the present disclosure and one or more other drugs are administered on different overlapping schedules. It is also contemplated that when used in combination with one or more other active ingredients, the compounds of the present disclosure and the other active ingredients may be used in lower doses than when each is used singly.

Accordingly, the pharmaceutical compositions of the present disclosure also include those that contain one or more other active ingredients, in addition to a compound of the present disclosure.

The above combinations include combinations of a compound of the present disclosure not only with one other active compound, but also with two or more other active compounds. Likewise, compounds of the present disclosure may be used in combination with other drugs that are used in the prevention, treatment, control, amelioration, or reduction of risk of the diseases or conditions for which compounds of the present disclosure are useful. Such other drugs may be administered, by a route and in an amount commonly used therefore, contemporaneously or sequentially with a compound of the present disclosure. When a compound of the present disclosure is used contemporaneously with one or more other drugs, a pharmaceutical composition containing such other drugs in addition to the compound of the present disclosure is preferred. Accordingly, the pharmaceutical compositions of the present disclosure also include those that also contain one or more other active ingredients, in addition to a compound of the present disclosure. The weight ratio of the compound of the present disclosure to the second active ingredient may be varied and will depend upon the effective dose of each ingredient. Generally, an effective dose of each will be used.

Where the patient in need is suffering from or at risk of suffering from an autoimmune disease, an inflammatory disease, or an allergy disease, a compound of the present disclosure can be used in with one or more of the following therapeutic agents in any combination: immunosuppressants (e.g., tacrolimus, cyclosporin, rapamicin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, celecoxib, or rofecoxib), leflunomide, gold thioglucose, gold thiomalate, aurofin, sulfasalazine, hydroxychloroquinine, minocycline, TNF-.alpha. binding proteins (e.g., infliximab, etanercept, or adalimumab), abatacept, anakinra, interferon-.beta., interferon-.gamma., interleukin-2, allergy vaccines, antihistamines, antileukotrienes, beta-agonists, theophylline, or anticholinergics.

Where the patient in need is suffering from or at risk of suffering from a proliferative disorder, the patient can be treated with a compound of the present disclosure in any combination with one or more other anti-cancer agents. In some embodiments, one or more of the anti-cancer agents are proapoptotic agents. Examples of anti-cancer agents include, but are not limited to, any of the following: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec™), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel", which is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with a compound of the present disclosure include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Other anti-cancer agents that can be employed in combination with a compound of the present disclosure include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-1a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with a compound of the present disclosure nclude: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; beta-clamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; fmasteride; flavopiridol; flezelastine; fluasterone; fludarabine; fluorodaunorubicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras famesyl protein transferase inhibitors; ras inhibitors; ras-GAP inhibitor; retelliptine demethylated; rhenium Re 186 etidronate; rhizoxin; ribozymes; R.sub.11 retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a compound of the present disclosure include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products useful in combination with a compound of the present disclosure include but are not limited to *vinca* alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination a compound of the present disclosure include, but are not limited to, nitrogen mustards (e.g., mechloroethamine, cyclophosphamide, chlorambucil, melphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites include, but are not limited to folic acid analog (e.g., methotrexate), or pyrimidine analogs (e.g., fluorouracil, floxuridine, Cytarabine), purine analogs (e.g., mercaptopurine, thioguanine, pentostatin.

Examples of hormones and antagonists useful in combination a compound of the present disclosure include, but are not limited to, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which can be used in combination with an irreversible Btk inhibitor compound include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin P E (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B. Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tularik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

The following preparations of compounds of Formula (I) and intermediates (References) are given to enable those skilled in the art to more clearly understand and to practice the present disclosure. They should not be considered as limiting the scope of the disclosure, but merely as being illustrative and representative thereof.

INTERMEDIATE 1

Synthesis of 2-bromo-5H-pyrrolo[2,3-b]pyrazine

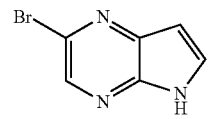

Step 1

A 500 ml three necked round bottom flask was charged with 3,5-dibromopyrazine-2-amine (25.0 g, 0.0988 mole) which was dissolved in acetonitrile (250 ml). The reaction mixture was cooled to 0° C. and triethylamine (50.0 g, 0.4941 mole), copper (1) iodide (2.26 g, 0.0119 mole), and Pd (PPh$_3$)$_4$ (5.7 g, 0.0049 mole) were added under nitrogen atmosphere. The reaction mixture was stirred for 10 min at 0° C. followed by slow addition of trimethylsilylacetylene (10.7 g, 0.1089 mole) over 15 min at the same temperature. After completion of the addition, the reaction mixture was warmed up to RT and stirred for 90 min. The reaction mixture was diluted by ethyl acetate and filtered. The filtrate was collected and washed with water. Layers were separated and aqueous layer was re-extracted by ethyl acetate. Combined organic layer was dried over Na$_2$SO$_4$, filtered and concentrated to afford crude product which was purified using column purification to afford 20.0 g of 5-bromo-3-((trimethylsilyl)ethynyl)pyrazine-2-amine.

Step 2

To a 250 ml flask, potassium tert-butoxide (4.2 g, 0.037 mole) was added followed by in THF (50 ml). To this, 5-bromo-3-((trimethylsilyl)ethynyl)pyrazine-2-amine (10.0 g, 0.037 mole) in THF (50 ml) was added dropwise at RT over 20 min under nitrogen atmosphere. The mixture was stirred 30 min at same temperature and 60 min at 65° C. The reaction mixture was cooled to RT and diluted with ethyl acetate and filtered. The filtrate was collected and washed with water. The layers were separated and the aq. layer was re-extracted with ethyl acetate. The combined organic layer was dried over Na$_2$SO$_4$, filtered, and concentrated to afford crude product which was was purified using column purification by eluting the compound with 15-20% ethyl acetate in hexanes to yield 4.3 g of 2-bromo-5H-pyrrolo[2,3-b]pyrazine.

INTERMEDIATE 2

Synthesis of 1-(2-(3-aminophenyl)-5H-pyrrolo[2,3-b]-pyrazin-7-yl)-2,2-dimethylpropan-1-one

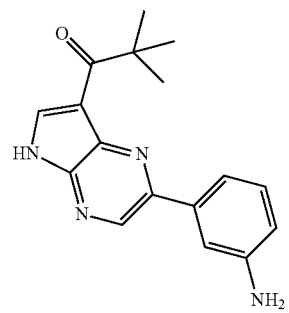 [SMILES: CC(C)(C)C(=O)c1c[nH]c2ncc(-c3cccc(N)c3)nc12]

Step 1

To a stirred solution of 2-bromo-5H-pyrrolo[2,3-b]pyrazine (5 g, 25.25 mmol) in 50 mL of dichloromethane at 0-5° C. was added diethyl aluminium chloride (1.0 M in hexane, 76 mL, 75.75 mmol). The reaction mixture was stirred at 0-5° C. for 30 min. Pivaloyl chloride (30.2 g, 252 mmol) was added to the reaction mixture and heated to reflux for 15 h. Saturated aqueous NaHCO$_3$ (100 mL) solution was added carefully and extracted with ethyl acetate. The organic layer was dried over Na$_2$SO$_4$, filtered and concentrated under reduced pressure. The crude product obtained was washed with diethyl ether to get 4.5 g (63%) of 1-(2-bromo-5H-pyrrolo[2,3-b]pyrazin-7-yl)-2,2-dimethylpropan-1-one as light yellow solid.

Step 2

To a stirred solution of 1-(2-bromo-5H-pyrrolo[2,3-b]pyrazin-7-yl)-2,2-dimethylpropan-1-one (600 mg, 2.133 mmol) in 1,4-dioxane was added 3-aminophenyl boronic acid (348 mg, 2.559 mmol), Pd(dppf)Cl$_2$ (519 mg, 0.633 mmol), potassium carbonate (879 mg, 6.39 mmol) under argon and heated to at 90° C. for 16 h. After completion of the reaction, the reaction mixture was diluted with water and extracted with ethyl acetate. The organic layer was separated and washed with brine solution. The organic layer was dried over Na$_2$SO$_4$, filtered and concentrated under reduced pressure. The crude product was purified by washing with diethyl ether to 190 mg (28%) of 1-(2-(3-aminophenyl)-5H-pyrrolo[2,3-b]pyrazin-7-yl)-2,2-dimethylpropan-1-one as yellow oil.

EXAMPLE 1

Synthesis of N-(3-(7-pivaloyl-5H-pyrrolo[2,3-b]pyrazin-2-yl)phenyl)acrylamide

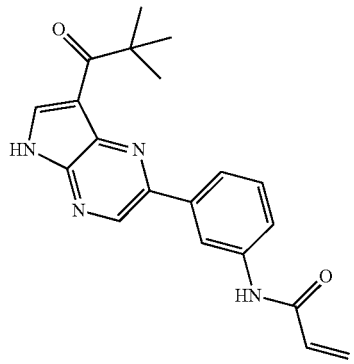 [SMILES: C=CC(=O)Nc1cccc(-c2cnc3[nH]cc(C(=O)C(C)(C)C)c3n2)c1]

To a stirred solution of 1-(2-(3-aminophenyl)-5H-pyrrolo[2,3-b]pyrazin-7-yl)-2,2-dimethylpropan-1-one (80 mg, 0.272 mmol) in N,N-dimethylacetamide was added acrylolyl chloride (18 mg, 0.259 mmol) and stirred at 50° C. for 2 h. After completion of the reaction, the reaction mixture was diluted with water and extracted with ethyl acetate. The organic layer was separated and washed with brine solution. The organic layer was dried over Na$_2$SO$_4$, filtered and concentrated under reduced pressure. The crude product was purified by prep TLC over SiO$_2$ GF-254 using 40% ethyl acetate in pet ether as gradient to get 30 mg (32%) of (N-(3-(7-pivaloyl-5H-pyrrolo[2,3-b]pyrazin-2-yl)phenyl)acrylamide as yellow solid. LC-MS: 98.07% (ES+APCI m/z: 349 (M+1).

INTERMEDIATE 3

Synthesis of 2-(3-aminophenyl)-N-tert-butyl-5-((2-(trimethylsilyl)ethoxy)methyl)-5H-pyrrolo[2,3-b]pyrazine-7-carboxamide

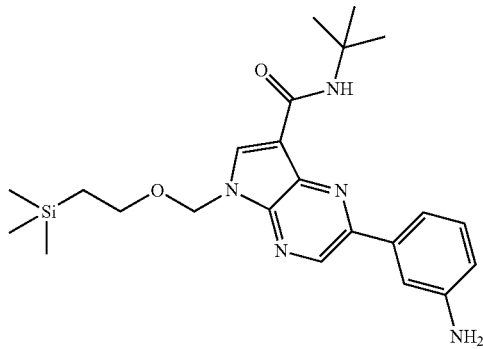 [SMILES: CC(C)(C)NC(=O)c1cn(COCC[Si](C)(C)C)c2ncc(-c3cccc(N)c3)nc12]

Step 1

To a reaction vial, 2-bromo-5H-pyrrolo[2,3-b]pyrazine (1 g, 5.05 mmol) was added in TFA (10 ml). Hexamine (1.06 g, 7.57 mmol) was added and reaction mixture was heated to 80° C. in, microwave for 15 min. After completion of the reaction, the reaction mixture was poured into aq. Na$_2$CO$_3$ solution. The solid obtained was filtered, dried and purified using column purification by eluting with 3-5% EtOAc in Hexanes to yield 0.450 g of 2-bromo-5H-pyrrolo[2,3-b]pyrazine-7-carbaldehyde.

Step 2

To a 10 ml round bottom flask, 2-bromo-5H-pyrrolo[2,3-b]pyrazine-7-carbaldehyde (0.450 g, 1.99 mmol) and NaH (0.143 g, 5.97 mmol) were taken in DMF (5 ml) and stirred in cooling for 15 min. SEM-Cl (0.497 g, 2.98 mmol) was added dropwise and stirred at rt for 2 h. After completion of the reaction, the reaction mixture was poured into water and extracted with ethyl acetate. The combined organics were washed with brine solution. The organic layer was separated and dried over sodium sulfate, concentrated to give the crude product which was purified using column purification by eluting the compound with 10% ethyl acetate in hexanes to yield 150 mg of 2-bromo-5-((2-(trimethylsilyl)ethoxy)methyl)-5H-pyrrolo[2,3-b]pyrazine-7-carbaldehyde.

Step 3

To a 25 ml round bottom flask, 2-bromo-5-((2-(trimethylsilyl)ethoxy)methyl)-5H-pyrrolo[2,3-b]pyrazine-7-carbaldehyde (0.1 g, 0.28 mmol) and sulfamic acid (0.163 g, 1.68 mmol) were taken in dioxane (1 ml) and water (0.1 ml). A solution of NaClO$_2$ (0.032 g, 0.36 mmol) and KH$_2$PO$_4$ (0.458 g, 3.36 mol) in water (0.9 ml) was added at 0° C. and the reaction mixture was stirred at room temperature for 2 h. After completion of the reaction, the reaction mixture was partitioned between water and ethyl acetate. The combined organics were washed with brine solution. The organic layer was separated and dried over sodium sulphate, concentrated to give 0.07 g of 2-bromo-5-((2-(trimethylsilyl)ethoxy)-methyl)-5H-pyrrolo[2,3-b]pyrazine-7-carboxylic acid which was used as such in next step.

Step 3

To a 25 ml round bottom flask, 2-bromo-5-((2-(trimethylsilyl)ethoxy)methyl)-5H-pyrrolo[2,3-b]pyrazine-7-carboxylic acid (2.2 g, 0.00591 mol), EDC.HCl (1.35 g, 7.09 mol), HOBt (0.958 g, 7.09 mmol), and DMAP (1.44 g, 0.0118 mol) were taken in DMF (20 ml) and stirred it for 15 min. tert-Butylamine (0.647 g, 8.87 mol) was added dropwise and the reaction mixture was stirred at room temperature overnight. After completion of the reaction, the reaction mixture was poured into water and extracted with ethyl acetate. The combined organics were washed with brine solution. The organic layer was separated and dried over sodium sulphate, concentrated to give the desired crude product which was purified using column purification by eluting the compound with 10% ethyl acetate in hexanes to yield 2.2 g of 2-bromo-N-tert-butyl-5-((2-(trimethylsilyl)ethoxy)methyl)-5H-pyrrolo[2,3-b]pyrazine-7-carboxamide.

Step 4

To a 35 ml microwave seal tube charged with 2-bromo-N-isopropyl-5-((2-(trimethyl-silyl)ethoxy)methyl)-5H-pyrrolo[2,3-b]pyrazine-7-carboxamide (0.30 g, 0.70 mmole) and 3-nitrophenylboronic acid (0.13 g, 0.7 mmole) was added dioxane: water (8:2 ml). To the reaction mass was added $PdCl_2(dppf)$ (0.046 g, 0.05 mmole), $K_2CO_3$ (0.241 g, 0.00175 mole) and the mixture degassed with $N_2$ gas for 15 min. The vial was sealed and heated in a microwave reactor at 150° C. for 45 min. The reaction mixture was cooled to RT, diluted with ethyl acetate and water and filtered. Layers from filtrate were separated and the aqueous phase was re-extracted by ethyl acetate. The combined organic layer was dried over $Na_2SO_4$, filtered and concentrated to afford crude product which was purified by chromatography.

The above process was repeated with additional 0.3 g and 0.4 g batches and the crude mixtures combined before purification. The combined material was purified using column purification to yield 0.95 g of N-tert-butyl-2-(3-nitrophenyl)-5-((2-(trimethylsilyl)ethoxy)methyl)-5H-pyrrolo[2,3-b]-pyrazine-7-carboxamide.

Step 5

In a 100 ml three necked round bottom flask, N-tert-butyl-2-(3-nitrophenyl)-5-((2-(trimethylsilyl)ethoxy)methyl)-5H-pyrrolo[2,3-b]-pyrazine-7-carboxamide (1.2 g, 2.5 mmole) was dissolved in methanol (35 ml). $SnCl_2$ (2.42 g, 0.013 mole) was added in portions at 0° C. to 5° C. under nitrogen atmosphere. After 15 min at the same temperature, the mixture was heated at reflux for 3 h. The reaction mixture was poured over saturated aqueous $NH_3$ and water (20 ml+100 ml) and filtered. The filtrate was collected, the layers were separated, and the aqueous phase was washed with $CH_2Cl_2$. The combined organic layer was dried over $Na_2SO_4$, filtered and concentrated to yield 0.9 g of 2-(3-aminophenyl)-N-tert-butyl-5-((2-(trimethylsilyl)ethoxy)-methyl)-5H-pyrrolo[2,3-b]pyrazine-7-carboxamide.

EXAMPLE 2

Synthesis of 2-(3-acrylamidophenyl)-N-(tert-butyl)-5H-pyrrolo[2,3-b]pyrazine-7-carboxamide

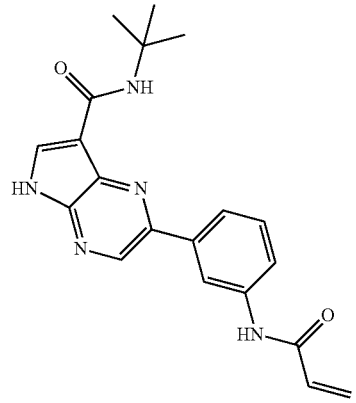 [SMILES: C=CC(=O)Nc1cccc(-c2cnc3[nH]cc(C(=O)NC(C)(C)C)c3n2)c1]

Step 1

In a 25 ml RBF, 2-(3-aminophenyl)-N-tert-butyl-5-((2-(trimethylsilyl)ethoxy)methyl)-5H-pyrrolo[2,3-b]pyrazine-7-carboxamide (0.150 g, 0.34 mmole) was taken up in $CH_2Cl_2$ (4 ml) and cooled to −30° C. under $N_2$ atm. To this, acroloyl chloride (0.025 ml in $CH_2Cl_2$, 3.0 mmole) was added dropwise to the reaction mass and stirred for 15 min. The mixture was made basic with saturated $NaHCO_3$ solution and extracted with $CH_2Cl_2$. The organic layer was dried over $Na_2SO_4$ and concentrated. The product was taken up in THF (2 ml), DBU (0.2 ml) was added and the reaction mixture stirred at rt for 16 h. Water was added to the reaction mixture and product was extracted with $CH_2Cl_2$. The organic layer was dried over $Na_2SO_4$ and evaporated to obtain a solid which was purified by triturating with pentane to yield 0.150 g of 2-(3-acryl-amidophenyl)-N-tert-butyl-5-((2-(trimethylsilyl)ethoxy)methyl)-5H-pyrrolo[2,3-b]pyrazine-7-carboxamide.

Step 2

To a 25 ml RBF, 2-(3-acrylamidophenyl)-N-tert-butyl-5-((2-(trimethylsilyl)ethoxy)-methyl)-5H-pyrrolo[2,3-b]pyrazine-7-carboxamide (0.1 g, 2 mmole) was taken up in $CH_2Cl_2$ (8 mL) and cooled to 0° C. under N2 atmosphere. TFA (2 ml) was added dropwise at 0° C. and stirred for 16 h at rt. The solvent was evaporated under reduced pressure from the reaction mixture. To this, saturated $NaHCO_3$ solution was added dropwise to make pH basic and the resultant precipitate was filtered out. The solid was washed with water and pentane and was then taken up in ethanol (20 ml) followed by addition of $NaOAc.3H_2O$ (0.275 g, 2.0 mmole) to reaction mixture. After stirring 16 h, ethanol was evaporated under reduced pressure from the reaction mixture and the obtained solid material was washed with water and pentane. The material was purified by triturating with pentane to yield 0.029 g of 2-(3-acrylamidophenyl)-N-tert-butyl-5H-pyrrolo[2,3-b]pyrazine-7-carboxamide. LC-MS (ES, m/z): 364.2 [M+H].

EXAMPLE 3

Synthesis of N-(tert-butyl)-2-(3-(4-(dimethylamino)but-2-enamido)phenyl)-5H-pyrrolo[2,3-b]pyrazine-7-carboxamide

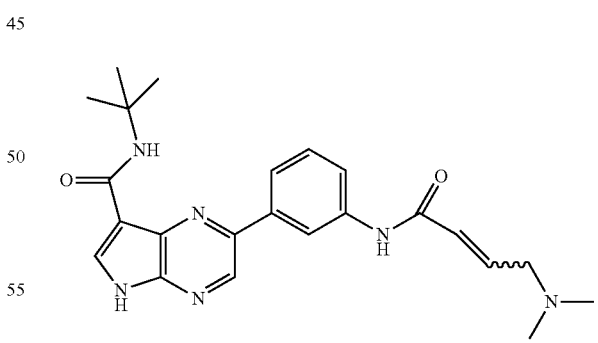

Step 1

To a 25 ml three necked round bottom flask, 2-(3-aminophenyl)-N-tert-butyl-5-((2-(trimethylsilyl)ethoxy)methyl)-5H-pyrrolo[2,3-b]pyrazine-7-carboxamide (0.3 g, 6.8 mmole) and 4-bromobut-2-enoic acid (0.13 g, 8.2 mmole) was taken in $CH_2Cl_2$ (10 ml). The reaction mass was cooled to 0° C. and 50% T3P in ethyl acetate (0.43 g, 1.36 mmole) was added dropwise followed by DIPEA (0.35 g, 2.72 mmole) dropwise at the same temperature under nitrogen atmosphere. The reaction mass was stirred for 1 h at 0° C. and then diluted with CH$_2$Cl$_2$ and water. The layers were separated and the aqueous layer was extracted by CH$_2$Cl$_2$. The combined organic layer was dried over Na$_2$SO$_4$, filtered and concentrated to yield 0.35 g of 2-3-(4-bromobut-2-enamido)phenyl)-N-tert-butyl-5-((2-(trimethylsilyl)ethoxy)methyl)-5H-pyrrolo[2,3-b]pyrazine-7-carboxamide.

Step 2

To a 10 ml single necked round bottom flask, 2-(3-(4-bromobut-2-enamido)phenyl)-N-tert-butyl-5-((2-(trimethylsilyl)ethoxy)methyl)-5H-pyrrolo[2,3-b]pyrazine-7-carboxamide (0.2 g, 0.34 mmole) was taken in THF (3 ml). To this, dimethylamine (2M in THF) (0.016 g, 0.34 mmole) and TEA (0.087 g, 0.85 mole) was added at rt under N$_2$ atmosphere. The reaction mass was stirred for 3 h at 50° C. and then water was added to the reaction mixture and the aqueous layer was extracted with ethyl acetate. The combined organic layer was dried over Na$_2$SO$_4$, filtered and concentrated to afford crude product. The crude compound was purified using column purification by eluting the compound with 5-8% methanol in CH$_2$Cl$_2$ to yield 0.090 g of N-tert-butyl-2-(3-(4-(dimethylamino)but-2-enamido)phenyl)-5-((2-(trimethylsilyl)ethoxy)-methyl)-5H-pyrrolo[2,3-b]pyrazine-7-carboxamide.

Step 3

A 25 ml round bottom flask was charged with N-tert-butyl-2-(3-(4-(dimethylamino)but-2-enamido)phenyl)-5-((2-(trimethylsilyl)ethoxy)methyl)-5H-pyrrolo[2,3-b]pyrazine-7-carboxamide (0.090 g, 0.1 mole) which was dissolved in CH$_2$Cl$_2$ (8 ml). To this reaction mass TFA (2.0 ml) was added dropwise at 0° C. under N$_2$ atmosphere and stirred at rt overnight. CH$_2$Cl$_2$ was distilled out and the mixture made basic by addition of saturated NaHCO$_3$ solution added at 5° C. The aqueous layer was extracted using CH$_2$Cl$_2$. The organic layer was dried over Na$_2$SO$_4$, filtered, and concentrated to afford the crude product. This was taken up in ethanol (15 ml) and NaAc.3H2O (0.222 g, 1.6 mmole) was added at RT. The reaction mass was stirred for 16 h at RT, diluted with ethyl acetate and the solvent removed under vacuum. The resultant residual solid was washed with water and filtered, followed by trituration with n-pentane. The solid was dried under vacuum to yield 45 mg of N-tert-butyl-2-(3-(4-(dimethylamino)but-2-enamido)phenyl)-5H-pyrrolo[2,3-b]pyrazine-7-carboxamide. LC-MS (ES, m/z): 421.3 [M+H].

BIOLOGICAL EXAMPLES

Example 1

JAK3 Caliper Peptide Phosphorylation Assay

Phosphorylation of the appropriate peptide substrate (fluorescently labeled Srctide) by recombinant JAK3 (catalytic domain, aa 781-1124) was measured in the presence and absence of different concentrations of test compounds. Test compound, enzyme, fluorescently labeled substrate, and cofactors (ATP and Mg$^{2+}$) were combined in a well of a microtiter plate and incubated for 2 hours at 25° C. The composition of the reaction buffer was 100 mM HEPES pH 7.5, 5 mM MgCl$_2$, 0.01% Triton-X 100, 0.1% Bovine Serum Albumin, and 1% DMSO. Enzyme concentration in the final reaction mixture was 0.5 nM while peptide substrate was at 1 uM. ATP was used at 1×Km concentration corresponding to 2 uM. Serial dilutions (3-fold steps) of compounds were prepared in DMSO. At the end of the incubation, the reaction was stopped by the addition of 20 mM EDTA. Substrate and product (i.e. phosphorylated substrate) were separated electrophoretically and both were quantified by fluorescence intensity using the microfluidics-based LabChip 3000 Drug Discovery System from Caliper Life Sciences. Conversion for each well was calculated and plotted as function of test compound concentration. IC$_{50}$ value was determined by fitting the data to a 4-parameter logistic model by non-linear regression (XLfit model 205). In every assay, Staurosporine was tested in the same manner as reference compound. Selectivity for JAK3 was determined using commercially available kinase cross-screening services (DiscoveRx, San Diego, Calif.).

The IC$_{50}$ of a representative number of compounds of the present disclosure is shown in Table below.

| CPD # | IC50 nm |
|---|---|
| 1 | 0.0025 |
| 2 | 0.0005 |
| 3 | 0.0035 |

Example 2

JAK3 TR-FRET Assay

Inhibition of JAK3 enzymatic activity by compounds is measured using time-resolved fluorescence resonance energy transfer (TR-FRET). Here, a signal is observed only when a Europium-coupled phosphotyrosine antibody binds the phosphorylated peptide. Test compounds are first prepared in 100% DMSO and serially diluted 10 times via 3-fold dilution. 2.5 ul of each serial dilution of the test compound at 4-fold the final assay concentration is next transferred to the 384-well assay plate (Corning Catalog #3676). A solution of 2-fold the final concentration of JAK3 enzyme (Invitrogen Catalog # PV3855) and Alexafluor 647-coupled peptide substrate (Invitrogen Catalog #5693) is next prepared in advance in a kinase buffer of 50 mM Hepes pH 7.5, 10 mM MgCl2, and 1 mM EGTA. For this solution, the final concentration of JAK3 and peptide is typically 1 nM and 100 nM, respectively. 5 uL of this 2-fold mix of JAK3 and peptide is added as the second step of the procedure to the 384-well assay plate. To initiate the enzymatic reaction, 2.5 ul of a 4-fold excess ATP solution in kinase buffer is added to the 384-well assay plate. Final ATP concentration is typically set to the Km for ATP. The reaction is allowed to proceed for 60 minutes. During the kinase reaction, a stop solution consisting of EDTA and a Europium-containing phosphotyrosine antibody (Invtrogen Catalog #5692) is prepared in TR-FRET dilution buffer (Invitrogen Catalog #3574). The stop solution contains an EDTA concentration of 20 mM and an antibody concentration of 4 nM. After the 60 minute, 10 ul of the stop solution is added to all wells. Each well is mixed and incubated for 30 minutes at room temperature. Plates are read on a Perkin Elmer Envision TR-FRET plate reader under LanthaScreen settings. Excitation wavelength is 337 nm and Emission wavelengths are 620 nm and 665 nm. Data are acquired as the ratio of emission at 665 nm/emission at 620 nm and plotted as a function of compound concentration to ascertain compound potency. Selectivity for JAK3 will be determined using commercially available kinase cross-screening services (DiscoveRx, San Diego, Calif.).

Example 3

Cellular JAK3 Activity Measured by Stat6 Reporter Assay in Ramos Cells

The beta lactamase-based select-screen reporter assay was used to measure JAK3 cell-based activity. The assay was preformed at Invitrogen. 32 µL of STAT6-bla RA1 (Invitrogen) cells diluted in Assay Media (OPTI-MEM, 0.5% dialyzed FBS, 0.1 mM NEAA, 1 mM sodium pyruvate, 100 U/ml/100 µg/ml Pen/Strep, 550 ng/ml CD40L) to 8×10$^6$ cells/ml cell density were added to the Poly-D-Lysine assay plate containing 4 µL of a 10× serial dilution of a JAK3 control compound (JAK inhibitor I (Calbiochem)) or test compounds. Pre-incubation at 37° C./5% CO$_2$ in a humidified incubator with test compound or control compound serial dilutions was for 30 minutes. 4 µL of 10× control activator IL-4 at the predetermined EC80 concentration was added to wells containing the control compound or test compound. The plate was incubated for 5 hours at 37° C./5% CO$_2$ in a humidified incubator. 8 µL of 1 µM Substrate Loading Solution consisting of Solution A (1 mM Live-BLAzer™-FRET B/G Substrate); Solution B (Invitrogen), and Solution C (Invitrogen), was added to each well and the plate was incubated for 2 hours at room temperature. The plate was read on a fluorescence plate reader and the data was analyzed. A response ratio was calculated from the emissions of cleaved and uncleaved substrate. The response ratio of wells with compound dilutions was compared with wells that contain only DMSO to calculate the percent inhibition at each compound concentration. A dose response curve was constructed and an IC$_{50}$ was calculated.

Example 4

Blockade of Stat5 Phosphorylation in Whole Blood or Peripheral Blood Mononuclear Cell (PBMC)

Activation of the IL-2 receptor leads to increased JAK3 activity, Stat5 phosphorylation and T cell activation (see O'Shea J. J, et. al. A new modality for immunosuppression: targeting the JAK/STAT pathway. *Nat Rev Drug Discov.* 3:555-64. 2004). JAK3 inhibitors have been shown to block T cell activation as measured by Stat5 phosphorylation (see Lin et al. Selective functional inhibition of Jak-3 is sufficient for efficacy in collagen-induced arthritis in mice. *Arthritis & Rheumatism* 62:2283-2293. 2010). Peripheral blood mononuclear cells (PBMC) were prepared from human whole blood by centrifugation on a ficoll gradient. Aliquots of PBMC were pre-incubated with serial dilutions of test compound for 30 minutes followed by activation with IL-2 (pre-determined EC80 concentration). Samples were incubated for 15 minutes and then fixed with 2% paraformaldehyde for PBMCs. Fixed cells were stained with Alexa647-labeled anti-phosphoStat5 pY694 antibodies (BD Biosciences) for 45 minutes. Stat5 phosphorylation was then analyzed by flow cytometry. The percent inhibition was calculated based on a DMSO control for no inhibition and plotted as a function of test compound concentration from which an IC$_{50}$ value was calculated.

Example 5

Inhibition of Mouse Collagen-induced Arthritis

Inhibition of murine collagen-induced arthritis (mCIA) is a standard animal disease model for rheumatoid arthritis. Previous studies have demonstrated that inhibition of JAK3 is efficacious in blocking mCIA (see Milici A. J, et al. Cartilage preservation by inhibition of Janus kinase 3 in two rodent models of rheumatoid arthritis. *Arthritis Res Ther.* 10:R14 1-9. 2008). Starting on day 0 DBA/1 mice are injected with an emulsion of Type II collagen in Complete Freund's Adjuvant. Mice are boosted 21 days later to synchronize development of disease. After development of mild disease, animals are enrolled in the study and randomized. Dosing is oral, Q.D. typically for 11 days with test compound or dexamethasone (0.2 mg/kg) as control. One group receives vehicle alone. Clinical scoring (0-4) is based on the extent of swelling and severity of arthritis. Scores for all four paws are added for maximum score of 16. Anti-collagen antibodies and total Ig are measured for each animal by ELISA at the end of the study (Bolder BioPath, Boulder, Colo.).

Example 6

Determination of Drug-Kinase Residence Time for JAK3

The following is a protocol to distinguish whether a compound displays a slow or non-existent dissociation rate from JAK3, such as typically would occur if a covalent bond is formed between the compound and the target. The readout for slow dissociation is the ability of the compound of interest to block binding of a high affinity fluorescent tracer molecule to the kinase active site, as detected using time-resolved fluorescence resonance energy transfer (TR-FRET). The experiment was conducted in a buffer consisting of 50 mM Hepes pH 7.5, 10 mM MgCl$_2$, 0.01% Triton X-100, and 1 mM EGTA.

The first step of the procedure was incubation of 500 nM JAK3 (Invitrogen Cat. #PV3855) with 1.5 uM of a compound disclosed in Table 1 for 30 minutes in a volume of 10 uL. The mixture was then diluted 5-fold by mixture of 10 uL JAK3/cmpd with 40 uL buffer. A 10 uL volume of the diluted kinase/compound solution was then added to a well of a small volume 384 well plate (such as Greiner Cat. #784076). In order to probe for reversibility of the kinase-compound binding interaction, a competition solution containing both a high affinity fluorescent tracer and an antibody coupled to Europium was prepared. For JAK3, the competition solution contained 8 uM Tracer 236 (Invitrogen Cat. #PV5592), which is a proprietary high affinity ligand for JAK3 coupled to the fluorophore AlexaFluor 647. The competition solution also contained 80 nM of an Anti-GST antibody coupled to Europium which is designed to bind the GST purification tag in JAK3.

After addition of 10 uL of the competition solution to the Greiner plate, the mixture was incubated for one hour or greater to allow time for dissociation of non-covalent inhibitors and binding of the high affinity tracer. It was expected that covalent and slow dissociating inhibitors will block binding of the tracer while rapidly dissociating non-covalent inhibitors will not. Binding of the tracer to JAK3 was detected using TR-FRET between the Europium moiety of the Anti-GST antibody and the AlexaFluor 647 group of Tracer 236. Binding was evaluated using a Perkin Elmer Envision instrument (Model 2101) equipped with filters and mirrors compatible with LANCE-type TR-FRET experiments. Data were plotted at percentage of signal obtained in the absence of competitor compound. The background signal was obtained by omission of JAK3 from the reaction. For compound 1, compound 2, and compound 3, no increase in binding of Tracer 236 was observed from 1 hour through 6 hours of the experiment, consistent with irreversible engagement of compound to JAK3.

Example 7

Reversibility of Binding

The following approach was developed to differentiate compounds that form irreversible bonds with their targets, such as acrylamide compounds, from compound that bind reversibly. Reactions were prepared with the JAK3 protein target at a higher concentration than the compound of interest. The reactions were then digested with trypsin, disrupting proper folding of the target. It has been found that digestion with trypsin returns reversible compounds to solution due to dissociation from the target while irreversible compounds remain bound to the target. The concentration of compound in solution was assessed both preceding and following perturbation using high performance liquid chromatography (HPLC) coupled to tandem mass spectrometry. Using this technique, it was demonstrated that an acrylamide-containing compound 1 (shown in table below) was depleted from solution in both the native and perturbed state (See table below) and hence is an irreversible inhibitor.

| Cpd | Compound in solution in the native state? | Compound in solution in the denatured or digested state? |
|---|---|---|
| 1 | no | no |

Example 8

Tumor Cell Proliferation Assay

Cells (SZ-4 CTCL cells) were plated at a density of 5000 cells/well (384 well plates). Cells were plated in DMEM culture media supplemented with 0.5% fetal bovine serum. Other tumor cells (e.g. NK-TCL, T-ALL) were plated at densities of 2000-10,000 cells/well in culture media (e.g. DMEM, RPMI), containing 1%-20% FBS, dependent on the growth requirements of the individual tumor cell line. Compounds were diluted in culture media using serial dilution yielding final concentrations with 0 (DMSO control) or concentrations ranging from 0.5 nM to 10 uM. For the CTCL cells, after 1 hr incubation, at 37° C. in 95% air, 5% $CO_2$, cells were induced with 100 ng/ml IL-2 for 72 hr. For the other cell types, cells were incubated without further induction for 72 hr. Cell Titer-Glo reagent was then added to the cells, contents mixed for 2 min, incubated at room temperature for 10 min, then luminescence was determined using a microplate luminometer. The percent inhibition was calculated based on a DMSO control for no inhibition and plotted as a function of test compound concentration from which an $IC_{50}$ value was calculated.

| Cell Line | Tumor Type and subtype if known | Cpd 2 $IC_{50}$ (µM) |
|---|---|---|
| SZ-4 | CTCL (Sézary syndrome) | 0.056 |
| Hut-102 | CTCL (Mycosis fungoides) | 0.104 |
| H9 | CTCL (Sézary syndrome) | 0.450 |
| H78 | CTCL (Sézary syndrome) | 0.150 |

-continued

| Cell Line | Tumor Type and subtype if known | Cpd 2 $IC_{50}$ (µM) |
|---|---|---|
| HH | CTCL (non MF, non Sézary syndrome) | 2.700 |
| MJ | CTCL (Unknown) | >5.00 |
| NKS1 | NK-TCL | 0.109 |
| KHG1 | NK-TCL | 0.498 |
| SNK1 | NK-TCL | 0.735 |
| SNK6 | NK-TCL | 8.42 |
| HANK1 | NK-TCL | 1.87 |

FORMULATION EXAMPLES

The following are representative pharmaceutical formulations containing a compound of Formula (I).

Tablet Formulation

The following ingredients are mixed intimately and pressed into single scored tablets.

| Ingredient | Quantity per tablet mg |
|---|---|
| compound of this disclosure | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule mg |
|---|---|
| compound of this disclosure | 200 |
| lactose spray dried | 148 |
| magnesium stearate | 2 |

Injectable Formulation

Compound of the disclosure (e.g., compound 1) in 2% HPMC, 1% Tween 80 in DI water, pH 2.2 with MSA, q.s. to at least 20 mg/ml The foregoing disclosure has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the disclosure should, therefore, be determined not with reference to the above description, but should instead be determined with reference to the following appended claims, along with the full scope of equivalents to which such claims are entitled.

What is claimed:

1. A compound of Formula (I):

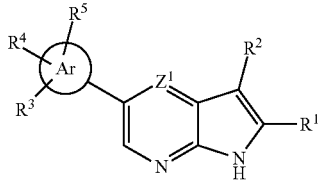

or a pharmaceutically acceptable salt thereof,
wherein:
$Z^1$ is N;
$R^1$ is hydrogen, alkyl, halo, haloalkyl, haloalkoxy, cyano, or cycloalkyl;
$R^2$ is hydrogen, alkyl, cycloalkyl, halo, cyano, acyl, aminocarbonyl, phenyl or heteroaryl, wherein each of phenyl and heteroaryl is optionally substituted with one, two or three substitutents independently chosen from alkyl, alkoxy, halo, haloalkyl, and haloalkoxy;
Ar is phenyl;
$R^3$ is attached to the phenyl ring at the meta position with respect to the

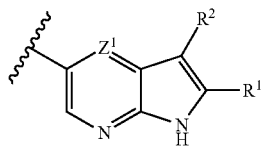

group and is -(alkylene)$_n$-Y—CH=CHR$^c$;
n is 0 or 1;
Y is —NR$^a$CO—, —NR$^a$SO$_2$—, —CO—, or —SO$_2$—;
$R^a$ is hydrogen or alkyl;
$R^c$ is hydrogen, alkyl, -alkylNH$_2$, -alkylNHalkyl, or -alkylN(alkyl)$_2$;
$R^4$ is hydrogen, alkyl, alkoxy, hydroxy, halo, haloalkyl, haloalkoxy, hydroxyalkyl, hydroxyalkoxy, alkoxyalkyl, alkoxyalkoxy, heterocyclylalkyl, heterocyclyloxy, heterocyclylalkoxy, aminoalkyl, or aminoalkoxy, wherein
the heterocyclylalkyl is optionally substituted with one or two substitutents independently chosen from alkyl, halo, hydroxyalkyl, and alkoxyalkyl;
the heterocyclyloxy is optionally substituted with one or two substitutents independently chosen from alkyl, halo, hydroxyalkyl, and alkoxyalkyl;
the heterocyclylalkoxy is optionally substituted with one or two substitutents independently chosen from alkyl, halo, hydroxyalkyl, and alkoxyalkyl; and
$R^5$ is hydrogen, alkyl, alkoxy, hydroxy, halo, haloalkyl, haloalkoxy, or cyano.

2. The compound of claim 1, or a pharmaceutically acceptable salt thereof, wherein $R^2$ is hydrogen, alkyl, cycloalkyl, halo, cyano, acyl, or aminocarbonyl.

3. The compound of claim 1, or a pharmaceutically acceptable salt thereof, wherein $R^2$ is acyl.

4. The compound of claim 1, or a pharmaceutically acceptable salt thereof, wherein $R^2$ is aminocarbonyl.

5. The compound of claim 1, or a pharmaceutically acceptable salt thereof, wherein $R^2$ is —CONHR', where R' is isopropyl, isobutyl, or tert-butyl.

6. The compound of claim 1, or a pharmaceutically acceptable salt thereof, wherein $R^4$ is hydrogen, alkyl, alkoxy, hydroxy, halo, haloalkyl, or haloalkoxy.

7. The compound of claim 6, or a pharmaceutically acceptable salt thereof, wherein $R^4$ is hydrogen, methyl, methoxy, fluoro, chloro, trifluoromethyl, or trifluoromethoxy.

8. The compound of claim 1, or a pharmaceutically acceptable salt thereof, wherein $R^4$ is hydroxyalkyl, hydroxyalkoxy, alkoxyalkyl, alkoxyalkoxy, heterocyclylalkyl, heterocyclyloxy, heterocyclylalkoxy, aminoalkyl, or aminoalkoxy, wherein
the heterocyclylalkyl is optionally substituted with one or two substitutents independently chosen from alkyl, halo, hydroxyalkyl, and alkoxyalkyl;
the heterocyclyloxy is optionally substituted with one or two substitutents independently chosen from alkyl, halo, hydroxyalkyl, and alkoxyalky; and
the heterocyclylalkoxy is optionally substituted with one or two substitutents independently chosen from alkyl, halo, hydroxyalkyl, and alkoxyalkyl.

9. The compound of claim 8, or a pharmaceutically acceptable salt thereof, wherein $R^4$ is hydroxyalkoxy, alkoxyalkoxy, heterocyclyloxy, heterocyclylalkoxy, or aminoalkoxy, wherein
the heterocyclyloxy is optionally substituted with one or two substitutents independently chosen from alkyl, halo, hydroxyalkyl, and alkoxyalkyl; and
the heterocyclylalkoxy is optionally substituted with one or two substitutents independently chosen from alkyl, halo, hydroxyalkyl, and alkoxyalkyl.

10. The compound of claim 9, or a pharmaceutically acceptable salt thereof, wherein $R^4$ is attached to the carbon meta to the carbon substituted with the $R^3$ group.

11. The compound of claim 1, or a pharmaceutically acceptable salt thereof, wherein $R^5$ is hydrogen.

12. The compound of claim 1, or a pharmaceutically acceptable salt thereof, wherein $R^c$ is hydrogen.

13. The compound of claim 1, or a pharmaceutically acceptable salt thereof, wherein $R^c$ is methyl.

14. The compound of claim 1, or a pharmaceutically acceptable salt thereof, wherein $R^c$ is -alkylNH$_2$, -alkylNHalkyl, or -alkylN(alkyl)$_2$.

15. The compound of claim 1, or a pharmaceutically acceptable salt thereof, wherein Y is —NHCO—.

16. The compound of claim 1, or a pharmaceutically acceptable salt thereof, wherein n is 0.

17. The compound of claim 1, or a pharmaceutically acceptable salt thereof, wherein n is 1.

18. The compound of claim 17, or a pharmaceutically acceptable salt thereof, wherein alkylene is methylene.

19. A pharmaceutical composition comprising a compound of claim 1, or a pharmaceutically acceptable salt thereof, and a pharmaceutically acceptable excipient.

20. A method of inhibiting Janus kinase 3 activity in a patient in need thereof, said method comprising administering to the patient in need thereof a pharmaceutical composition comprising a therapeutically effective amount a compound of claim 1, or a pharmaceutically acceptable salt thereof, and a pharmaceutically acceptable excipient.

21. The method of claim 20, wherein the patient suffers from a disease chosen from an autoimmune disease, an inflammatory disease, and cancer.

22. The method of claim 21, wherein the cancer is cutaneous T-cell lymphoma or natural killer T-cell lymphoma.

23. The method of claim 21, wherein the compound is administered optionally in combination with one or more anticancer or anti-inflammatory agents.

24. A compound chosen from:
   N-(3-(7-pivaloyl-5H-pyrrolo[2,3-b]pyrazin-2-yl)phenyl) acrylamide;
   2-(3-acrylamidophenyl)-N-(tert-butyl)-5H-pyrrolo[2,3-b]pyrazine-7-carboxamide; and
   N-(tert-butyl)-2-(3-(4-(dimethylamino)but-2-enamido)phenyl)-5H-pyrrolo[2,3-b]-pyrazine-7-carboxamide,
   an E or Z stereoisomer of any of the foregoing compounds, or
   a pharmaceutically acceptable salt thereof.

* * * * *

UNITED STATES PATENT AND TRADEMARK OFFICE
CERTIFICATE OF CORRECTION

PATENT NO. : 9,676,778 B2  
APPLICATION NO. : 14/443705  
DATED : June 13, 2017  
INVENTOR(S) : David Michael Goldstein et al.

Page 1 of 1

It is certified that error appears in the above-identified patent and that said Letters Patent is hereby corrected as shown below:

In the Claims

Claim 8, Column 42, Lines 10-11, "heterocvclylalkyl" should read -- heterocyclylalkyl --.

Signed and Sealed this  
Third Day of October, 2017

Joseph Matal  
*Performing the Functions and Duties of the*  
*Under Secretary of Commerce for Intellectual Property and*  
*Director of the United States Patent and Trademark Office*